United States Patent
Crouzet et al.

[11] Patent Number: 6,143,530
[45] Date of Patent: Nov. 7, 2000

[54] CIRCULAR DNA EXPRESSION CASSETTES FOR IN VIVO GENE TRANSFER

[75] Inventors: Joël Crouzet, Sceaux; Daniel Scherman, Paris; Béatrice Cameron, Paris; Pierre Wils, Paris; Anne-Marie Darquet, Vitry sur Seine, all of France

[73] Assignee: Rhone-Poulenc Rorer S.A., Antony, France

[21] Appl. No.: 08/894,511

[22] PCT Filed: Feb. 21, 1996

[86] PCT No.: PCT/FR96/00274

§ 371 Date: Aug. 19, 1997

§ 102(e) Date: Aug. 19, 1997

[87] PCT Pub. No.: WO96/26270

PCT Pub. Date: Aug. 29, 1996

[30] Foreign Application Priority Data

Feb. 23, 1995 [FR] France ................................. 95 02117

[51] Int. Cl.[7] ........................... C12N 15/64; C12N 15/79; C12N 15/70; C12N 1/21; C12N 5/10
[52] U.S. Cl. .................... 435/91.42; 435/91.1; 435/91.4; 435/320.1; 435/325; 435/252.3; 435/252.33; 435/254.11; 435/455; 514/44
[58] Field of Search .......................... 514/44; 435/320.1, 435/325, 252.3, 252.33, 254.11, 91.1, 91.4, 91.42, 455

[56] References Cited

U.S. PATENT DOCUMENTS 5,227,288  7/1993  Blattner ........................................ 435/6
5,401,632  3/1995  Wang et al. ................................. 435/6

FOREIGN PATENT DOCUMENTS 300 422  1/1989  European Pat. Off. ..
350 341  1/1990  European Pat. Off. ..
WO 94/09127  4/1994  WIPO .
WO 96/05297  2/1996  WIPO .

OTHER PUBLICATIONS

Takabatake et al., The use of purine–rich oligonucleotides in triplex–mediated DNA isolation and generation of unidirectional deletions, Nucletic Acids Research, 20(21), 5853–5854 (1992).

Ito et al., Sequence–specific DNA purification by triplex affinity capture, Proc. Natl. Acad. Sci. USA, 89, 495–498 (1992).

Mizuuchi et al., The extent of DNA sequence required for a functional bacterial attachment site of phage lambda, Nucleic–Acids Research, 13(4) 1193–1208 (1985).

Hasan et al., Control of cloned gene expression by promoter inversion in vivo: construction of improved vectors with a multiple cloning site and the ptac promoter, Gene, 56, 145–151 (1987).

Su et al., Selective Binding of *Escherichia coli* RNA Polymerase to Topoisomers of Minicircles Carrying the TAC16 and TAC17 Promoters, Journal of Biological Chemistry 269(18), 13511–13521 (1994).

Backman et al., Use of Synchronous Site–Specific Recombination In Vivo To Regulate Gene Expression, Biotechnology, 2(12) 1045–1049 (1984).

Eberl et al., Analysis of the multimer resolution system encoded by the parCBA operon of broad–host–range plasmid RP4, Molecular Microbiology 12(1), 131–141 (1994).

Stark et al., Catalysis by site–specific recombinases, Trenda in Genetics, 8(12), 432–439 (1992).

Orkin et al., "Report and recommendations of the panel to assess the NIH investment in research on gene therapy", issued by the U.S. National Institutes of Health, Dec. 1995.

Ben–Yedidia et al., "Design of peptide and polypeptide vaccines", Curr. Opin. Biotechnol. 8: 442–448, Aug. 1997.

*Primary Examiner*—Scott D. Priebe
*Attorney, Agent, or Firm*—Finnegan, Henderson, Farabow, Garrett & Dunner, L.L.P.

[57] ABSTRACT

Double-stranded DNA molecules characterised in that they are circular and in that they essentially include one or more genes of interest.

43 Claims, 11 Drawing Sheets

CIRCULAR DNA EXPRESSION CASSETTES FOR IN VIVO GENE TRANSFER

Gene therapy consists in correcting a deficiency or an abnormality by introducing genetic information into the affected cell or organ. This information may be introduced either in vitro into a cell extracted from the organ and then reinjected into the body, or in vivo, directly into the tissue concerned. Being a high molecular weight, negatively charged molecule, DNA has difficulties in passing spontaneously through the phospholipid cell membranes. Different vectors are hence used in order to permit gene transfer: viral vectors on the one hand, natural or synthetic, chemical and/or biochemical vectors on the other hand. Viral vectors (retroviruses, adenoviruses, adeno-associated viruses, etc.) are very effective, in particular in passing through membranes, but present a number of risks, such as pathogenicity, recombination, replication, immunogenicity, etc. Chemical and/or biochemical vectors enable these risks to be avoided (for reviews, see Behr, 1993, Cotten and Wagner, 1993). These vectors are, for example, cations (calcium-phosphate, DEAE-dextran, etc.) which act by forming precipitates with DNA, which precipitates can be "phagocytosed" by the cells. They can also be liposomes in which DNA is incorporated and which fuse with the plasma membrane. Synthetic gene transfer vectors are generally lipids or cationic polymers which complex DNA and form a particle therewith carrying positive surface charges. These particles are capable of interacting with the negative charges of the cell membrane and then of crossing the latter. Dioctadecylamidoglycylspermine (DOGS, Transfectam™) or N-[1-(2,3-dioleyloxy)propyl]-N,N,N-trimethylammonium chloride (DOTMA, Lipofectin™) may be mentioned as examples of such vectors. Chimeric proteins have also been developed: they consist of a polycationic portion which condenses DNA, linked to a ligand which binds to a membrane receptor and carries the complex into the cells by endocytosis. It is thus theoretically possible to "target" a tissue or certain cell populations so as to improve the in vivo bioavailability of the transferred gene.

However, the use of chemical and/or biochemical vectors or of naked DNA implies the possibility of producing large amounts of DNA of pharmacological purity. In effect, in these gene therapy techniques, the medicinal product consists of the DNA itself, and it is essential to be able to manufacture, in appropriate amounts, DNAs having suitable properties for therapeutic use in man.

The plasmids currently used in gene therapy carry (i) an origin of replication, (ii) a marker gene such as a gene for resistance to an antibiotic (kanamycin, ampicillin, etc.) and (iii) one or more transgenes with sequences required for their expression (enhancer(s), promoter(s), polyadenylation sequences, etc.). These plasmids currently used in gene therapy (in clinical trials such as the treatment of melanomas, Nabel et al., 1992, or in experimental studies) display, however, some drawbacks associated, in particular, with their dissemination in the body. Thus, as a result of this dissemination, a competent bacterium present in the body can, at a low frequency, receive this plasmid. The chance of this occurring is all the greater for the fact that the treatment in question entails in vivo gene therapy in which the DNA may be disseminated in the patient's body and may come into contact with bacteria which infect this patient or alternatively with bacteria of the commensal flora. If the bacterium which is a recipient of the plasmid is an enterobacterium such as E. coli, this plasmid may replicate. Such an event then leads to the dissemination of the therapeutic gene.

Inasmuch as the therapeutic genes used in gene therapy treatments can code, for example, for a lymphokine, a growth factor, an anti-oncogene, or a protein whose function is lacking in the host and hence enables a genetic defect to be corrected, the dissemination of some of these genes could have unforeseeable and worrying effects (for example if a pathogenic bacterium were to acquire the gene for a human growth factor). Furthermore, the plasmids used in non-viral gene therapy also possess a marker for resistance to an antibiotic (ampicillin, kanamycin, etc.). Hence the bacterium acquiring such a plasmid has an undeniable selective advantage, since any therapeutic antibiotic treatment using an antibiotic of the same family as the one selecting the resistance gene of the plasmid will lead to the selection of the plasmid in question. In this connection, ampicillin belongs to the β-lactams, which is the family of antibiotics most widely used in the world. It is hence necessary to seek to limit as far as possible the dissemination of the therapeutic genes and the resistance genes. Moreover, the genes carried by the plasmid, corresponding to the vector portion of the plasmid (function(s) required for replication, resistance gene), also run the risk of being expressed in the transfected cells. There is, in effect, a transcription background, which cannot be ruled out, due to the host's expression signals on the plasmid. This expression of exogenous proteins may be thoroughly detrimental in a number of gene therapy treatments, as a result of their potential immunogenicity and hence of the attack of the transfected cells by the immune system.

Hence it is especially important to be able to have at one's disposal medicinal DNA molecules having a genetic purity suitable for therapeutic use. It is also especially important to have at one's disposal methods enabling these DNA molecules to be prepared in amounts appropriate for pharmaceutical use. The present invention provides a solution to these problems.

The present invention describes, in effect, DNA molecules which can be used in gene therapy, having greatly improved genetic purity and impressive properties of bioavailability. The invention also describes an especially effective method for the preparation of these molecules and for their purification.

The present invention lies, in particular, in the development of DNA molecules which can be used in gene therapy, virtually lacking any non-therapeutic region. The DNA molecules according to the invention, also designated minicircles on account of their circular structure, their small size and their supercoiled form, display many advantages.

They make it possible, in the first place, to eliminate the risks associated with dissemination of the plasmid, such as (1) replication and dissemination which may lead to an uncontrolled overexpression of the therapeutic gene, (2) the dissemination and expression of resistance genes, and (3) the expression of genes present in the non-therapeutic portion of the plasmid, which are potentially immunogenic and/or inflammatory, and the like. The genetic information contained in the DNA molecules according to the invention is limited, in effect, essentially to the therapeutic gene(s) and to the signals for regulation of its/their expression (neither origin of replication, nor gene for resistance to an antibiotic, and the like). The probability of these molecules (and hence of the genetic information they contain) being transferred to a microorganism and being stably maintained is almost zero.

Furthermore, due to their small size, DNA molecules according to the invention potentially have better bioavailability in vivo. In particular, they display improved capacities for cell penetration and cellular distribution. Thus, it is recognized that the coefficient of diffusion in the tissues is inversely proportional to the molecular weight (Jain, 1987). Similarly, at cellular level, high molecular weight molecules have inferior permeability through the plasma membrane. In addition, for the plasmid to progress to the nucleus, which is essential for its expression, high molecular weight is also a drawback, the nuclear pores imposing a size limit for diffusion to the nucleus (Landford et al., 1986). The elimination of the non-therapeutic portions of the plasmid (origin of replication and resistance gene in particular) according to the invention also enables the size of the DNA molecules to be decreased. This decrease may be estimated at a factor of 2, reckoning, for example, 3 kb for the origin of replication and the resistance marker (vector portion) and 3 kb for the transgene with the sequences required for its expression. This decrease (i) in molecular weight and (ii) in negative charge endows the molecules of the invention with improved capacities for tissue, cellular and nuclear diffusion and bioavailability.

Hence a first subject of the invention lies in a double-stranded DNA molecule having the following features: it is circular in shape and essentially comprises one or more genes of interest. As stated above, the molecules of the invention essentially lack non-therapeutic regions, and especially an origin of replication and/or a marker gene. In addition, they are advantageously in supercoiled form.

The present invention is also the outcome for the development of a method, of constructions and of cell hosts which are specific and especially effective for the production of these therapeutic DNA molecules. More especially, the method according to the invention lies in the production of therapeutic DNA molecules defined above, by excision from a plasmid or from a chromosome by site-specific recombination. The method according to the invention is especially advantageous, since it does not necessitate a prior step of purification of the plasmid, is very specific, especially effective, does not decrease the amounts of DNA produced and leads directly to therapeutic molecules of very great genetic purity and of great bioavailability. This method leads, in effect, to the generation of circular DNA molecules (minicircles) essentially containing the gene of interest and the regulator sequences permitting its expression in the cells, tissue, organ or apparatus, or even the whole body, in which the expression is desired. In addition, these molecules may then be purified by standard techniques.

The site-specific recombination may be carried out by means of various systems which lead to site-specific recombination between sequences. More preferably, the site-specific recombination in the method of the invention is obtained by means of two specific sequences which are capable of recombining with one another in the presence of a specific protein, generally designated recombinase. For this reason, the DNA molecules according to the invention generally comprise, in addition, a sequence resulting from this site-specific recombination. The sequences permitting the recombination used in the context of the invention generally comprise from 5 to 100 base pairs, and more preferably fewer than 50 base pairs.

The site-specific recombination may be carried out in vivo (that is to say in the host cell) or in vitro (that is to say on a plasmid preparation).

In this connection, the present invention also provides particular genetic constructions suitable for the production of the therapeutic DNA molecules defined above. These genetic constructions, or recombinant DNAs, according to the invention comprise, in particular, the gene or genes of interest flanked by the two sequences permitting site-specific recombination, positioned in the direct orientation. The position in the direct orientation indicates that the two sequences follow the same 5'-3' polarity in the recombinant DNA according to the invention. The genetic constructions of the invention can be double-stranded DNA fragments (cassettes) essentially composed of the elements mentioned above. These cassettes can be used for the construction of cell hosts having these elements integrated in their genome (FIG. 1). The genetic constructions of the invention can also be plasmids, that is to say any linear or circular DNA molecule capable of replicating in a given host cell, containing the gene or genes of interest flanked by the two sequences permitting site-specific recombination, positioned in the direct orientation. The construction can be, more specifically, a vector (such as a cloning and/or expression vector), a phage, a virus, and the like. These plasmids of the invention may be used to transform any competent cell host for the purpose of the production of minicircles by replication of the plasmid followed by excision of the minicircle (FIG. 2).

In this connection, another subject of the invention lies in a recombinant DNA comprising one or more genes of interest, flanked by two sequences permitting site-specific recombination, positioned in the direct orientation.

The recombinant DNA according to the invention is preferably a plasmid comprising at least:

a) an origin of replication and optionally a marker gene,
b) two sequences permitting a site-specific recombination, positioned in the direct orientation, and,
c) placed between said sequences b), one or more genes of interest.

The specific recombination system present in the genetic constructions according to the invention can be of different origins. In particular, the specific sequences and the recombinases used can belong to different structural classes, and in particular to the integrase family of bacteriophage λ or to the resolvase family of the transposon Tn3.

Among recombinases belonging to the integrase family of bacteriophage λ, there may be mentioned, in particular, the integrase of the phages lambda (Landy et al., Science 197 (1977) 1147), P22 and Φ80 (Leong et al., J. Biol. Chem. 260 (1985) 4468), HP1 of *Haemophilus influenza* (Hauser et al., J. Biol. Chem. 267 (1992) 6859), the Cre integrase of phage P1, the integrase of the plasmid pSAM2 (EP 350,341) or alternatively the FLP recombinase of the 2μ plasmid. When the DNA molecules according to the invention are prepared by recombination by means of a site-specific system of the integrase family of bacteriophage lambda, the DNA molecules according to the invention generally comprise, in addition, a sequence resulting from the recombination between two att attachment sequences of the corresponding bacteriophage or plasmid.

Among recombinases belonging to the family of the transposon Tn3, there may be mentioned, in particular, the resolvase of the transposon Tn3 or of the transposons Tn21 and Tn522 (Stark et al., 1992); the Gin invertase of bacteriophage mu or alternatively the resolvase of plasmids, such as that of the par fragment of RP4 (Albert et al., Mol. Microbiol. 12 (1994) 131). When the DNA molecules according to the invention are prepared by recombination by means of a site-specific system of the family of the transposon Tn3, the DNA molecules according to the invention generally comprise, in addition, a sequence resulting from the recombination between two recognition sequences of the resolvase of the transposon in question.

According to a particular embodiment, in the genetic constructions of the present invention, the sequences permitting site-specific recombination are derived from a bacteriophage. More preferably, these latter are attachment sequences (attP and attB sequences) of a bacteriophage, or derived sequences. These sequences are capable of recombining specifically with one another in the presence of a recombinase designated integrase. The term derived sequence includes the sequences obtained by modification(s) of the attachment sequences of the bacteriophages, which retain the capacity to recombine specifically in the presence of the appropriate recombinase. Thus, such sequences can be reduced fragments of these sequences or, on the contrary, fragments extended by the addition of other sequences (restriction sites, and the like). They can also be variants obtained by mutation(s), in particular by point mutation(s). The terms attP and attB sequences of a bacteriophage or of a plasmid denote, according to the invention, the sequences of the recombination system specific to said bacteriophage or plasmid, that is to say the attP sequence present in said phage or plasmid and the corresponding chromosomal attB sequence.

By way of preferred examples, there may be mentioned, in particular, the attachment sequences of the phages lambda, P22, Φ80, P1 and HP1 of *Haemophilus influenzae* or alternatively of plasmid pSAM2 or the 2μ plasmid. These sequences are advantageously chosen from all or part of the sequences SEQ ID No. 1, SEQ ID No. 2, SEQ ID No. 6, SEQ ID No. 7, SEQ ID No. 8, SEQ ID No. 9, SEQ ID No. 10, SEQ ID No. 11, SEQ ID No. 12, SEQ ID No. 13 and SEQ ID No. 14. These sequences comprise, in particular, the central region homologous to the attachment sequences of these phages.

In this connection, a preferred plasmid according to the present invention comprises (a) a bacterial origin of replication and optionally a marker gene, (b) the attP and attB sequences of a bacteriophage selected from the phages lambda, P22, Φ80, HP1 and P1 or of plasmid pSAM2 or the 2μ plasmid, or derived sequences; and, (c) placed between said sequences b), one or more genes of interest.

According to an especially preferred embodiment, the sequences in question are the attachment sequences (attP and attB) of phage lambda. Plasmids carrying these sequences are, in particular, the plasmids pXL2648, pXL2649 or pXL2650. When these plasmids are brought, in vivo or in vitro, into contact with the integrase of phage lambda, the sequences recombine with one another to generate in vivo or in vitro, by excision, a minicircle according to the invention essentially comprising the elements (c), that is to say the therapeutic portion (FIG. 2).

Still according to a particular embodiment of the invention, the sequences permitting site-specific recombination are derived from the loxP region of phage P1. This region is composed essentially of two inverted repeat sequences capable of recombining specifically with one another in the presence of a protein, designated Cre (Sternberg et al., J. Mol. Biol. 150 (1971) 467). In a particular variant, the invention hence relates to a plasmid comprising (a) a bacterial origin of replication and optionally a marker gene; (b) the inverted repeat sequences of bacteriophage P1 (loxP region); and (c), placed between said sequences (b), one or more genes of interest.

According to another particular embodiment, in the genetic constructions of the present invention, the sequences permitting site-specific recombination are derived from a transposon. More preferably, the sequences in question are recognition sequences of the resolvase of a transposon, or derived sequences. By way of preferred examples, there may be mentioned, in particular, the recognition sequences of the transposons Tn3, Tn21 and Tn522. By way of a preferred example, there may be mentioned the sequence SEQ ID No. 15 or a derivative of the latter (see also Sherrat, P. 163–184, Mobile DNA, Ed. D. Berg and M. Howe, American Society for Microbiology, Washington D.C. 1989).

According to another especially advantageous variant, the plasmids of the invention comprise, in addition, a multimer resolution sequence. This is preferably the mrs (multimer resolution system) sequence of the plasmid RK2. More preferably, the invention relates to a plasmid comprising:

(a) a bacterial origin of replication and optionally a marker gene, (b) the attP and attB sequences of a bacteriophage, in the direct orientation, selected from the phages lambda, P22, Φ80, HP1 and P1 or of plasmid pSAM2 or the 2μ plasmid, or derived sequences; and, (c) placed between said sequences b), one or more genes of interest and the mrs sequence of plasmid RK2.

This embodiment is especially advantageous. Thus, when plasmids pXL2649 or pXL2650 are brought into contact with the integrase of the bacteriophage in vivo, the sequences recombine to generate the minicircle and the miniplasmid, but also multimeric or topological forms of minicircle or of miniplasmid. It is especially advantageous to be able to decrease the concentration of these forms in order to increase the production and facilitate the purification of minicircle.

The multimeric forms of plasmids are known to a person skilled in the art. For example, the cer fragment of ColE1 (Summers et al., 1984 Cell 36 p. 1097) or the mrs site of the par locus of RK2 (L. Ebert 1994 Mol. Microbiol. 2 p. 131) permit the resolution of multimers of plasmids and participate in an enhanced stability of the plasmid. However, whereas resolution at the cer site requires four proteins encoded by the *E. coli* genome (Colloms et al., 1990 J. Bacteriol. 172 p. 6973), resolution at the mrs site requires only the ParA protein for which the parA gene is mapped on the par locus of RK2. As a result, it would appear advantageous to use all or a portion of the par locus containing parA and the mrs sequence. For example, the mrs sequence may be placed between the attB and attP sequences of phage lambda, and the parA gene be expressed in trans or in cis from its own promoter or from an inducible promoter. In this connection, a particular plasmid of the invention comprises:

(a) a bacterial origin of replication and optionally a marker gene, (b) the attP and attB sequences of a bacteriophage, in the direct orientation, selected from the phages lambda, P22, Φ80, HP1 and P1 or of plasmid pSAM2 or the 2μ plasmid, or derived sequences, (c) placed between said sequences b), one or more genes of interest and the mrs sequence of plasmid RK2, and (d) the parA gene of plasmid RK2.

One such plasmid is, in particular, the plasmid pXL2960 described in the examples. It may be employed, and can enable minicircle to be produced exclusively in monomeric form.

According to another advantageous variant, the plasmids of the invention comprise two sets of site-specific recombination sequences from a different family. These advantageously comprise a first set of integrase-dependent sequences and a second set of parA-dependent sequences. The use of two sets of sequences enables the production yields of minicircles to be increased when the first site-specific recombination is incomplete. Thus, when plasmids pXL2650 or pXL2960 are brought into contact with the integrase of the bacteriophage in vivo, the sequences recombine to generate the miniplasmid and the minicircle, but this reaction is not complete (5 to 10% of initial plasmid may be left). The introduction, in proximity to each of the att sequences of phage lambda, of an mrs sequence of RK2 enables the production of minicircles to be increased. Thus, after induction of the integrase of phage lambda and Int-dependent recombination, the unrecombined molecules will be able to come under the control of the ParA protein of RK2 and to recombine at the mrs sites. Conversely, after induction of the ParA protein and ParA-dependent recombination, the unrecombined molecules will be able to come under the control of the integrase of phage lambda and will be able to recombine at the att sites. Such constructions thus make it possible to produce minicircle and negligible amounts of unrecombined molecules. The att sequences, like the mrs sequences, are in the direct orientation, and the int and parA genes may be induced simultaneously or successively from the same inducible promoter or from two inducible promoters. Preferably, the sequences in question are the attB and attP attachment sequences of phage lambda in the direct orientation and two mrs sequences of RK2 in the direct orientation.

As stated above, another aspect of the present invention lies in a method for the production of therapeutic DNA molecules defined above, by excision, from a plasmid or chromosome, by site-specific recombination.

Another subject of the present invention hence lies in a method for the production of a DNA molecule (minicircle) as defined above, according to which a culture of host cells containing a recombinant DNA as defined above is brought into contact with the recombinase enabling site-specific recombination to be induced. More preferably, the culture and recombinase are brought into contact either by transfection or infection with a plasmid or a phage containing the gene for said recombinase; or by induction of the expression of a gene coding for said recombinase, present in the host cell. As mentioned below, this gene may be present in the host cell in integrated form in the genome, on a replicative plasmid or alternatively on the plasmid of the invention, in the non-therapeutic portion.

To permit the production of the minicircles according to the invention by site-specific recombination in vivo, the recombinase used must be introduced into, or induced in, cells or the culture medium at a particular instant. For this purpose, different methods may be used. According to a first method, a host cell is used containing the recombinase gene in a form permitting its regulated expression. It may, in particular, be introduced under the control of a promoter or of a system of inducible promoters, or alternatively in a temperature-sensitive system. In particular, the gene may be present in a temperature-sensitive phage, latent during the growth phase, and induced at a suitable temperature (for example lysogenic phage lambda Xis⁻ cI857). The cassette for expression of the recombinase gene may be carried by a plasmid, a phage or even by the plasmid of the invention, in the non-therapeutic region. It may be integrated in the genome of the host cell or maintained in replicative form. According to another method, the cassette for expression of the gene is carried by a plasmid or a phage used to transfect or infect the cell culture after the growth phase. In this case, it is not necessary for the gene to be in a form permitting its regulated expression. In particular, any constitutive promoter may be used. The cell may also be brought into contact with the recombinase in vitro, on a plasmid preparation, by direct incubation with the protein.

It is preferable, in the context of the present invention, to use a host cell capable of expressing the recombinase gene in a regulated manner. This embodiment, in which the recombinase is supplied directly by the host cell after induction, is especially advantageous. In effect, it suffices simply to place the cells in culture at the desired time under the conditions for expression of the recombinase gene (permissive temperature for a temperature-sensitive gene, addition of an inducer for a regulable promoter, and the like) in order to induce the site-specific recombination in vivo and thus the excision of the minicircle of the invention. In addition, this excision takes place in especially high yields, since all the cells in culture express the recombinase, which is not necessarily the case if a transfection or an infection has to be carried out in order to transfer the recombinase gene.

According to a first embodiment, the method of the invention comprises the excision of the molecules of therapeutic DNA by site-specific recombination from a plasmid. This embodiment employs the plasmids described above permitting, in a first stage, replication in a chosen host, and then, in a second stage, the excision of the non-therapeutic portions of said plasmid (in particular the origin of replication and the resistance gene) by site-specific recombination, generating the circular DNA molecules of the invention. To carry out the method, different types of plasmid may be used, and especially a vector, a phage or a virus. A replicative vector is preferably used.

Advantageously, the method of the invention comprises a prior step of transformation of host cells with a plasmid as defined above, followed by culturing of the transformed cells, enabling suitable amounts of plasmid to be obtained. Excision by site-specific recombinations is then carried out by bringing into contact with the recombinase under the conditions defined above (FIG. 2). As stated above, in this embodiment, the site-specific recombination may be carried out in vivo. (that is to say in the host cell) or in vitro (that is to say on a plasmid preparation).

According to a preferred embodiment, the DNA molecules of the invention are hence obtained from a replicative vector, by excision of the non-therapeutic portion carrying, in particular, the origin of replication and the marker gene, by site-specific recombination.

According to another embodiment, the method of the invention comprises the excision of the DNA molecules from the genome of the host cell by site-specific recombination. This embodiment is based more especially on the construction of cell hosts comprising, inserted into their genome, one or more copies of a cassette comprising the gene of interest flanked by the sequences permitting recombination (FIG. 1). Different techniques may be used for insertion of the cassette of the invention into the genome of the host cell. In particular, insertion at several distinct points of the genome may be obtained by using integrative vectors. In this connection, different transposition systems such as, in particular, the miniMu system or defective transposons such as Tn10 derivatives, for example, may be used (Kleckner et al., Methods Enzymol. 204 (1991) 139; Groisman E., Methods Enzymol. 204 (1991) 180). The insertion may also be carried out by homologous recombination, enabling a cassette containing two recombination sequences in the direct orientation flanking one or more genes of interest to be integrated in the genome of the bacterium. This process may, in addition, be reproduced as many times as desired so as to have the largest possible number of copies per cell. Another technique also consists in using an in vivo amplification system using recombination, as described in Labarre et al. (Labarre J., O. Reyes, Guyonvarch, and G. Leblon. 1993. Gene replacement, integration, and amplification at the gdhA locus of *Corynebacterium glutamicum*. J. Bacteriol. 175:1001–107), so as to augment from one copy of the cassette to a much larger number.

A preferred technique consists in the use of miniMu. To this end, miniMu derivatives are constructed comprising a resistance marker, the functions required in cis for their transposition and a cassette containing two recombination sequences in the direct orientation flanking the gene or genes of interest. These miniMus are advantageously placed at several points of the genome using a resistance marker (kanamycin, for example) enabling several copies per genome to be selected (Groisman E. cited above). As described above, the host cell in question can also express inducibly a site-specific recombinase leading to the excision of the fragment flanked by the recombination sequences in the direct orientation. After excision, the minicircles may be purified by standard techniques.

This embodiment of the method of the invention is especially advantageous, since it leads to the generation of a single type of plasmid molecule: the minicircle of the invention. The cells do not contain, in effect, any other episomal plasmid, as is the case during production from a plasmid (FIGS. 1 and 2).

Another subject of the invention also lies in a modified host cell comprising, inserted into its genome, one or more copies of a recombinant DNA as defined above.

The invention also relates to any recombinant cell containing a plasmid as defined above. These cells are obtained by any technique known to a person skilled in the art enabling a DNA to be introduced into a given cell. Such a technique can be, in particular, transformation, electroporation, conjugation, protoplast fusion or any other technique known to a person skilled in the art. As regards transformation, different protocols have been described in the prior art. In particular, cell transformation may be carried out by treating whole cells in the presence of lithium acetate and polyethylene glycol according to the technique described by Ito et al. (J. Bacteriol. 153 (1983) 163–168), or in the presence of ethylene glycol and dimethyl sulphoxide according to the technique of Durrens et al. (Curr. Genet. 18 (1990) 7). An alternative protocol has also been described in Patent Application EP 361,991. As regards electroporation, this may be carried out according to Becker and Guarentte (in: Methods in Enzymology Vol194 (1991) 182).

The method according to the invention may be carried out in any type of cell host. Such hosts can be, in particular, bacteria or eukaryotic cells (yeasts, animal cells, plant cells), and the like. Among bacteria, *E.coli*, *B. subtilis*, Streptomyces, Pseudomonas (*P. putida*, *P. aeruginosa*), *Rhizobium meliloti*, *Agrobacterium tumefaciens*, *Staphylococcus aureus*, *Streptomyces pristinaespiralis*, *Enterococcus faecium* or Clostridium, and the like, may be mentioned more preferentially. Among bacteria, it is preferable to use *E.coli*. Among yeasts, Kluyveromyces, Saccharomyces, Pichia, Hansenula, and the like, may be mentioned. Among mammalian animal cells, CHO, COS, NIH3T3, and the like, cells may be mentioned.

In accordance with the host used, the plasmid according to the invention is adapted by a person skilled in the art to permit its replication. In particular, the origin of replication and the marker gene are chosen in accordance with the host cell selected.

The marker gene may be a resistance gene, in particular for resistance to an antibiotic (ampicillin, kanamycin, geneticin, hygromycin, and the like), or any gene endowing the cell with a function which it no longer possesses (for example a gene which has been deleted on the chromosome or rendered inactive), the gene on the plasmid reestablishing this function.

In a particular embodiment, the method of the invention comprises an additional step of purification of the minicircle.

In this connection, the minicircle may be purified by standard techniques of plasmid DNA purification, since it is supercoiled like plasmid DNA. These techniques comprise, inter alia, purification on a cesium chloride density gradient in the presence of ethidium bromide, or alternatively the use of anion exchange columns (Maniatis et al., 1989). In addition, if the plasmid DNA corresponding to the non-therapeutic portions (origin of replication and selectable marker in particular) is considered to be present in an excessively large amount, it is also possible, after or before the purification, to use one or more restriction enzymes which will digest the plasmid and not the minicircle, enabling them to be separated by techniques that separate supercoiled DNA from linear DNA, such as a cesium chloride density gradient in the presence of ethidium bromide (Maniatis et al., 1989).

In addition, the present invention also describes an improved method for the purification of minicircles. This method enables minicircles of very great purity to be obtained in large yields in a single step. This improved method is based on the interaction between a double-stranded sequence present in the minicircle and a specific ligand. The ligand can be of various natures, and in particular protein, chemical or nucleic acid in nature. It is preferably a ligand of the nucleic acid type, and in particular an oligonucleotide, optionally chemically modified, capable of forming by hybridization a triple helix with the specific sequence present in the DNA molecule of the invention. It was, in effect, shown that some oligonucleotides were capable of specifically forming triple helices with double-stranded DNA sequences (Hélène et al., Biochim. Biophys. Acta 1049 (1990) 99; see also FR 94/15162 incorporated in the present application by reference).

In an especially advantageous variant, the DNA molecules of the invention hence contain, in addition, a sequence capable of interacting specifically with a ligand (FIG. 3). Preferably, it is a sequence capable of forming, by hybridization, a triple helix with a specific oligonucleotide. This sequence may be positioned at any site of the DNA molecule of the invention, provided it does not affect the functionality of the gene of interest. This sequence is also present in the genetic constructions of the invention (plasmids, cassettes), in the portion containing the gene of interest (see, in particular, the plasmid pXL2650). Preferably, the specific sequence present in the DNA molecule of the invention comprises between 5 and 30 base pairs.

The oligonucleotides used for carrying out the method according to the invention can contain the following bases:
thymidine (T), which is capable of forming triplets with A.T doublets of double-stranded DNA (Rajagopal et al., Biochem 28 (1989) 7859);
adenine (A), which is capable of forming triplets with A.T doublets of double-stranded DNA;
guanine (G), which is capable of forming triplets with G.C doublets of doubled-stranded DNA;
protonated cytosine (C+), which is capable of forming triplets with G.C doublets of doubled-stranded DNA (Rajagopal et al., cited above).

Preferably, the oligonucleotide used comprises a homopyrimidine sequence containing cytosines, and the specific sequence present in the DNA molecule is a homopurine-homopyrimidine sequence. The presence of cytosines makes it possible to have a triple helix which is stable at acid pH where the cytosines are protonated, and destabilized at alkaline pH where the cytosines are neutralized.

To permit the formation of a triple helix by hybridization, it is important for the oligonucleotide and the specific sequence present in the DNA molecule of the invention to be complementary. In this connection, to obtain the best yields and best selectivity, an oligonucleotide and a specific sequence which are fully complementary are used in the method of the invention. Possible combinations are, in particular, a poly(CTT) oligonucleotide and a poly(GAA) specific sequence. By way of example, there may be mentioned the oligonucleotide of sequence GAGGCTTCTTCT-TCTTCTTCTTCTT (SEQ ID No. 5), in which the bases GAGG do not form a triple helix but enable the oligonucleotide to be spaced apart from the coupling arm.

It is understood, however, that some mismatches may be tolerated, provided they do not lead to too great a loss of affinity. The oligonucleotide used may be natural (composed of unmodified natural bases) or chemically modified. In particular, the oligonucleotide may advantageously possess some chemical modifications enabling its resistance or its protection against nucleases, or its affinity for the specific sequence, to be increased.

Thus, the oligonucleotide may be rendered more resistant to nucleases by modification of the skeleton (e.g. methylphosphonates, phosphorothiates, phosphotriester, phosphoramidate, and the like). Another type of modification has as its objective, more especially, to improve the interaction and/or the affinity between the oligonucleotide and the specific sequence. In particular, a thoroughly advantageous modification according to the invention consists in methylating the cytosines of the oligonucleotide. The oligonucleotide thus methylated displays the noteworthy property of forming a stable triple helix with the specific sequence at neutral pH. Hence it makes it possible to work at higher pH values than the oligonucleotides of the prior art, that is to say at pH values where the risks of degradation of the plasmid DNA are lower.

The length of the oligonucleotide used in the method of the invention is at least 3 bases, and preferably between 5 and 30. An oligonucleotide of length greater than 10 bases is advantageously used. The length may be adapted to each individual case by a person skilled in the art in accordance with the desired selectivity and stability of the interaction.

The oligonucleotides according to the invention may be synthesized by any known technique. In particular, they may be prepared by means of nucleic acid synthesizers. It is quite obvious that any other method known to a person skilled in the art may be used.

To carry out the method of the invention, the specific ligand (protein, nucleic acid, and the like) may be grafted or otherwise onto a support. Different types of supports may be used for this purpose, such as, in particular, functionalized chromatography supports, in bulk form or prepacked in columns, functionalized plastic surfaces or functionalized latex beads, magnetic or otherwise. Chromatography supports are preferably used. By way of example, the chromatography supports which may be used are agatose, acrylamide or dextran, as well as their derivatives (such as Sephadex, Sepharose, Superose, etc.), polymers such as poly(styrenedivinylbenzene), or grafted or ungrafted silica, for example. The chromatography columns can function in the diffusion or perfusion mode.

To permit its covalent coupling to the support, the ligand is generally functionalized. In the case of an oligonucleotide, this may be modified, for example, with a terminal thiol, amine or carboxyl group at the 5' or 3' position. In particular, the addition of a thiol, amine or carboxyl group makes it possible, for example, to couple the oligonucleotide to a support carrying disulphide, maleimide, amine, carboxyl, ester, epoxide, cyanogen bromide or aldehyde functions. These couplings form by the establishment of disulphide, thioether, ester, amide or amine links between the oligonucleotide and the support. Any other method known to a person skilled in the art may be used, such as bifunctional coupling reagents, for example.

Moreover, to improve the activity of the coupled oligonucleotide, it may be advantageous to perform the coupling by means of an "arm". Use of an arm makes it possible, in effect, to bind the oligonucleotide at a chosen distance from the support, enabling its conditions of interaction with the DNA molecule of the invention to be improved. The arm advantageously consists of nucleotide bases that do not interfere with the hybridization. Thus, the arm may comprise purine bases. By way of example, the arm may comprise the sequence GAGG.

The DNA molecules according to the invention may be used in any application of vaccination or of gene and cell therapy, for the transfer of a gene to a body, a tissue or a given cell. In particular, they may be used for a direct administration in vivo, or for the modification of cells in vitro or ex vivo with a view to their implantation in a patient. In this connection, the molecules according to the invention may be used as they are (in the form of naked DNA), or in combination with different synthetic or natural, chemical and/or biochemical vectors. The latter can be, in particular, cations (calcium phosphate, DEAE-dextran, etc.) which act by forming precipitates with DNA, which precipitates can be "phagocytosed" by the cells. They can also be liposomes in which the DNA molecule is incorporated and which fuse with the plasma membrane. Synthetic gene transfer vectors are generally lipids or cationic polymers which complex DNA and form a particle therewith carrying positive surface charges. These particles are capable of interacting with the negative charges of the cell membrane and then of crossing the latter. DOGS (Transfectam™) or DOTMA (Lipofectin™) may be mentioned as examples of such vectors. Chimeric proteins have also been developed: they consist of a polycationic portion which condenses DNA, linked to a ligand which binds to a membrane receptor and carries the complex into the cells by endocytosis. The DNA molecules according to the invention may also be used for gene transfer into cells by physical transfection techniques such as bombardment, electroporation, and the like. In addition, prior to their therapeutic use, the molecules of the invention may optionally be linearized, for example by enzymatic cleavage.

In this connection, another subject of the present invention relates to any pharmaceutical composition comprising at least one DNA molecule as defined above. This molecule may be naked or combined with a chemical and/or biochemical transfection vector. The pharmaceutical compositions according to the invention may be formulated with a view to topical, oral, parenteral, intranasal, intravenous, intramuscular, subcutaneous, intra-ocular, transdermal, and the like, administration. Preferably, the DNA molecule is used in an injectable form or by application. It may be mixed with any pharmaceutically acceptable vehicle for an injectable formulation, in particular for a direct injection at the site to be treated. The compositions can be, in particular, in the form of isotonic sterile solutions, or of dry, in particular lyophilized compositions which, on addition of sterilized water or physiological saline as appropriate, enable injectable solutions to be made up. Diluted Tris or PBS buffers in glucose or sodium chloride may be used in particular. A direct injection of the nucleic acid into the affected region of the patient is advantageous, since it enables the therapeutic effect to be concentrated in the tissues affected. The doses of nucleic acid used may be adapted in accordance with different parameters, and in particular in accordance with the gene, the vector, the mode of administration used, the pathology in question or alternatively the desired treatment period.

The DNA molecules of the invention may contain one or more genes of interest, that is to say one or more nucleic acids (cDNA, gDNA, synthetic or semi-synthetic DNA, and the like) whose transcription and, where appropriate, translation in the target cell generate products of therapeutic, vaccinal, agricultural or veterinary value.

Among the genes of therapeutic value, there may be mentioned, more especially, the genes coding for enzymes, blood derivatives, hormones, lymphokines, namely interleukins, interferons, TNF, and the like (FR 92/03120), growth factors, neurotransmitters or their precursors or synthetic enzymes, trophic factors, namely BDNF, CNTF, NGF, IGF, GMF, aFGF, bFGF, NT3, NT5, and the like; apolipoproteins, namely ApoAI, ApoAIV, ApoE, and the like (FR 93/05125), dystrophin or a minidystrophin (FR 91/11947), tumour suppressive genes, namely p53, Rb, Rap1A, DCC, k-rev, and the like (FR 93/04745), genes coding for factors involved in coagulation, namely factors VII, VIII, IX, and the like, suicide genes, namely thymidine kinase, cytosine deaminase, and the like; or alternatively all or part of a natural or artificial immunoglobulin (Fab, ScFv, and the like), a ligand RNA (WO91/19813), and the like. The therapeutic gene can also be an antisense gene or sequence whose expression in the target cell enables gene expression or the transcription of cellular mRNAs to be controlled. Such sequences can, for example, be transcribed in the target cell into RNAs complementary to cellular mRNAs, and can thus block their translation into protein, according to the technique described in Patent EP 140,308.

The gene of interest can also be a vaccinating gene, that is to say a gene coding for an antigenic peptide, capable of generating an immune response in man or animals for the purpose of vaccine production. Such antigenic peptides can be, in particular, those specific to the Epstein-Barr virus, the HIV virus, the hepatitis B virus (EP 185,573) or the pseudorabies virus, or alternatively tumour-specific peptides (EP 259,212).

Generally, in the plasmids and molecules of the invention, the gene of therapeutic, vaccinal, agricultural or veterinary value also contains a transcription promoter region which is functional in the target cell or body (i.e. mammals), as well as a region located at the 3' end and which specifies a transcription termination signal and a polyadenylation site (expression cassette). As regards the promoter region, this can be a promoter region naturally responsible for the expression of the gene in question when the latter is capable of functioning in the cell or body in question. The promoter regions can also be those of different origin (responsible for the expression of other proteins, or even synthetic promoters). In particular, the promoter sequences can be from eukaryotic or viral genes. For example, they can be promoter sequences originating from the genome of the target cell. Among eukaryotic promoters, it is possible to use any promoter or derived sequence that stimulates or represses the transcription of a gene, specifically or otherwise, inducibly or otherwise, strongly or weakly. They can be, in particular, ubiquitous promoters (promoter of the HPRT, PGK, α-actin, tubulin, and the like, genes), promoters of intermediate filaments (promoter of the GFAP, desmin, vimentin, neurofilament, keratin, and the like, genes), promoters of therapeutic genes (for example the promoter of the MDR, CFTR, factor VIII, ApoAI, and the like, genes), tissue-specific promoters (promoter of the pyruvate kinase gene, villin gene, gene for intestinal fatty acid binding protein, gene for α-actin of smooth muscle, and the like) or alternatively promoters that respond to a stimulus (steroid hormone receptor, retinoic acid receptor, and the like). Similarly, the promoter sequences may be those originating from the genome of a virus, such as, for example, the promoters of the adenovirus E1A and MLP genes, the CMV early promoter or alternatively the RSV LTR promoter, and the like. In addition, these promoter regions may be modified by the addition of activator or regulator sequences or sequences permitting a tissue-specific or -preponderant expression.

Moreover, the gene of interest can also contain a signal sequence directing the synthesized product into the pathways of secretion of the target cell. This signal sequence can be the natural signal sequence of the product synthesized, but it can also be any other functional signal sequence, or an artificial signal sequence.

Depending on the gene of interest, the DNA molecules of the invention may be used for the treatment or prevention of a large number of pathologies, including genetic disorders (dystrophy, cystic fibrosis, and the like), neurodegenerative diseases (Alzheimer's, Parkinson's, ALS, and the like), cancers, pathologies associated with disorders of coagulation or with dyslipoproteinaemias, pathologies associated with viral infections (hepatitis, AIDS, and the like), or in the agricultural and veterinary fields, and the like.

The present invention will be described more completely by means of the examples which follow, which are to be regarded as illustrative and non-limiting.

Figure 1:
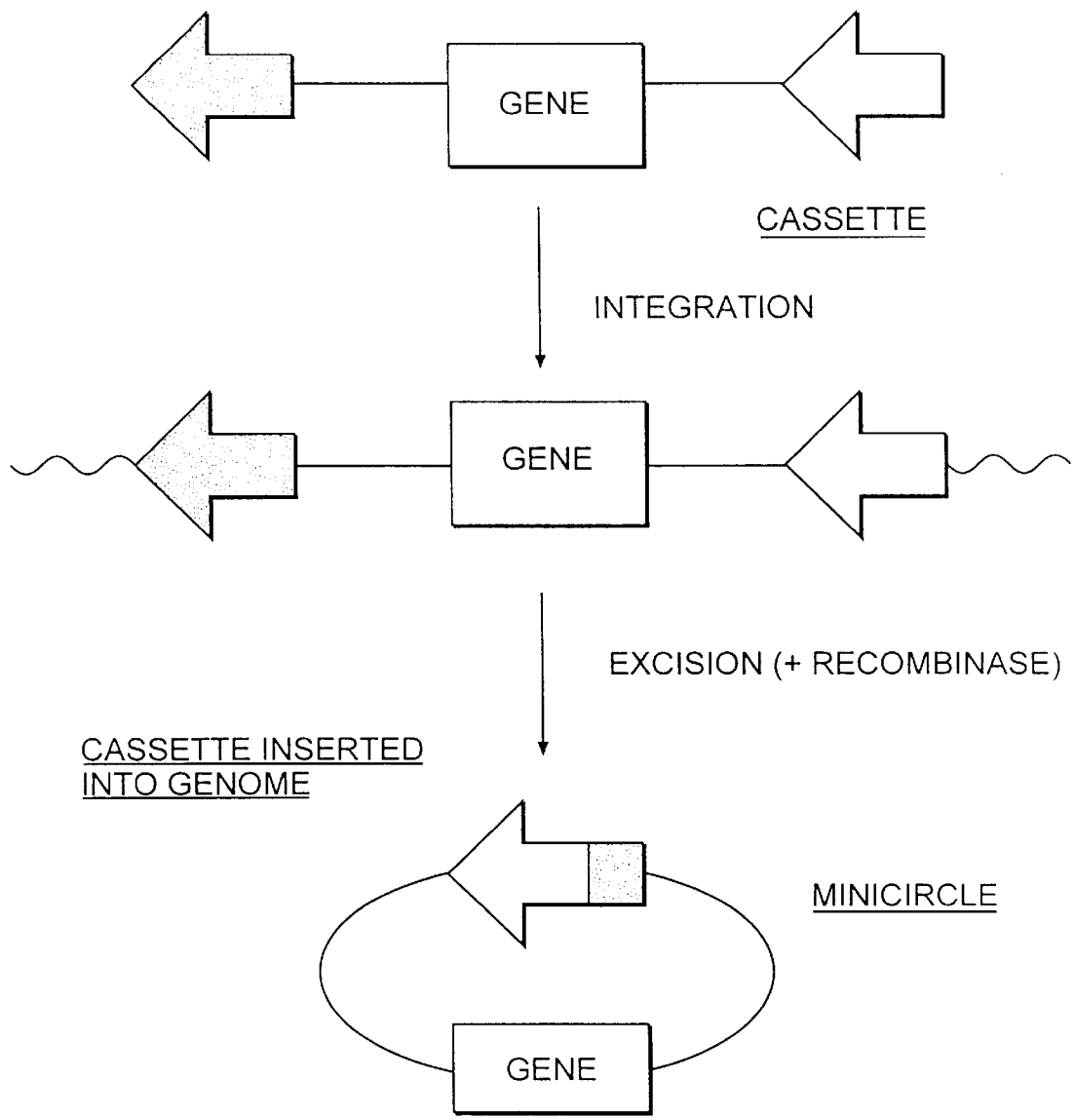
FIG. 1: Production of a minicircle from a cassette integrated in the genome.
Figure 2:
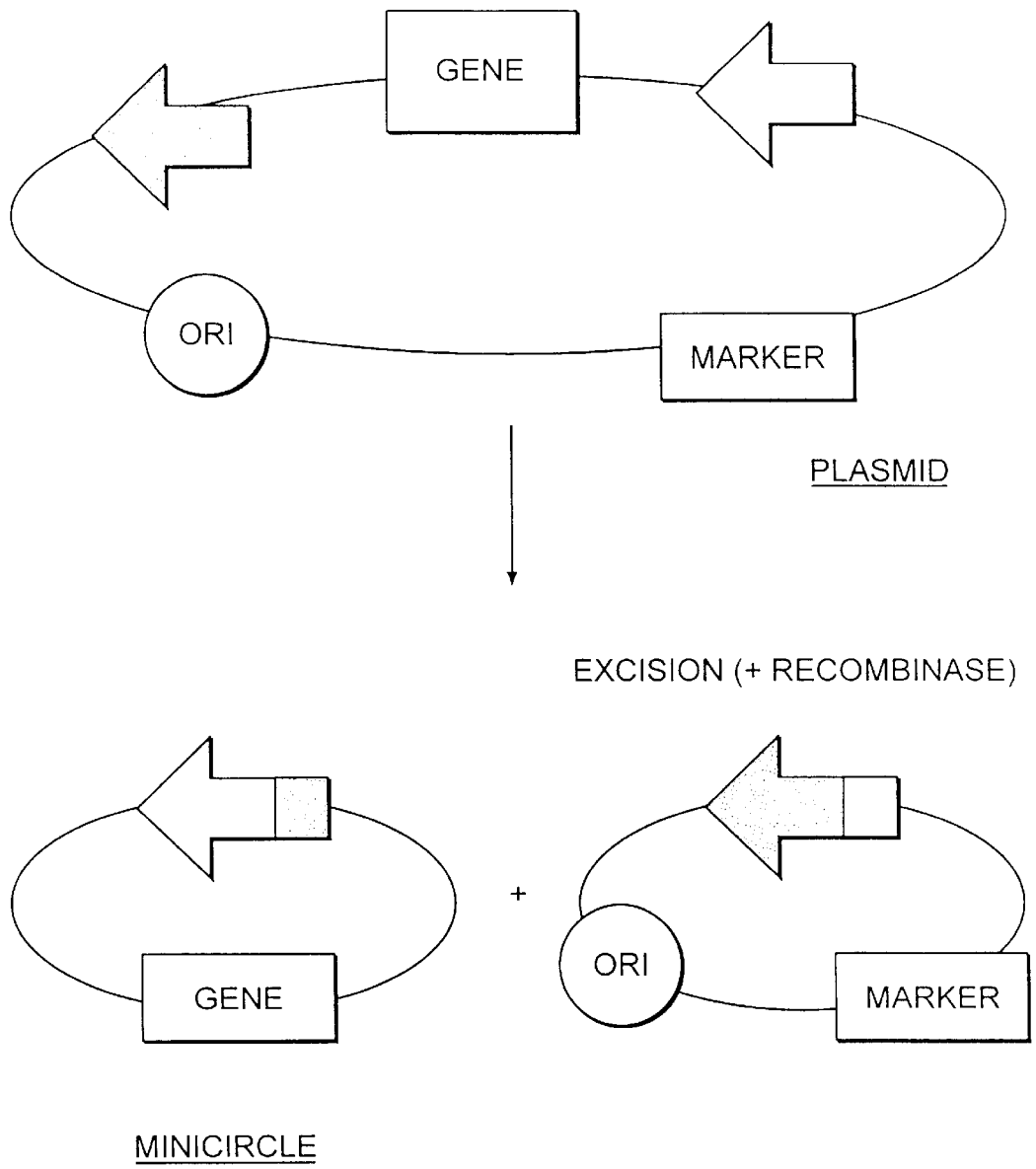
FIG. 2: Production of a minicircle from a plasmid.
Figure 3:
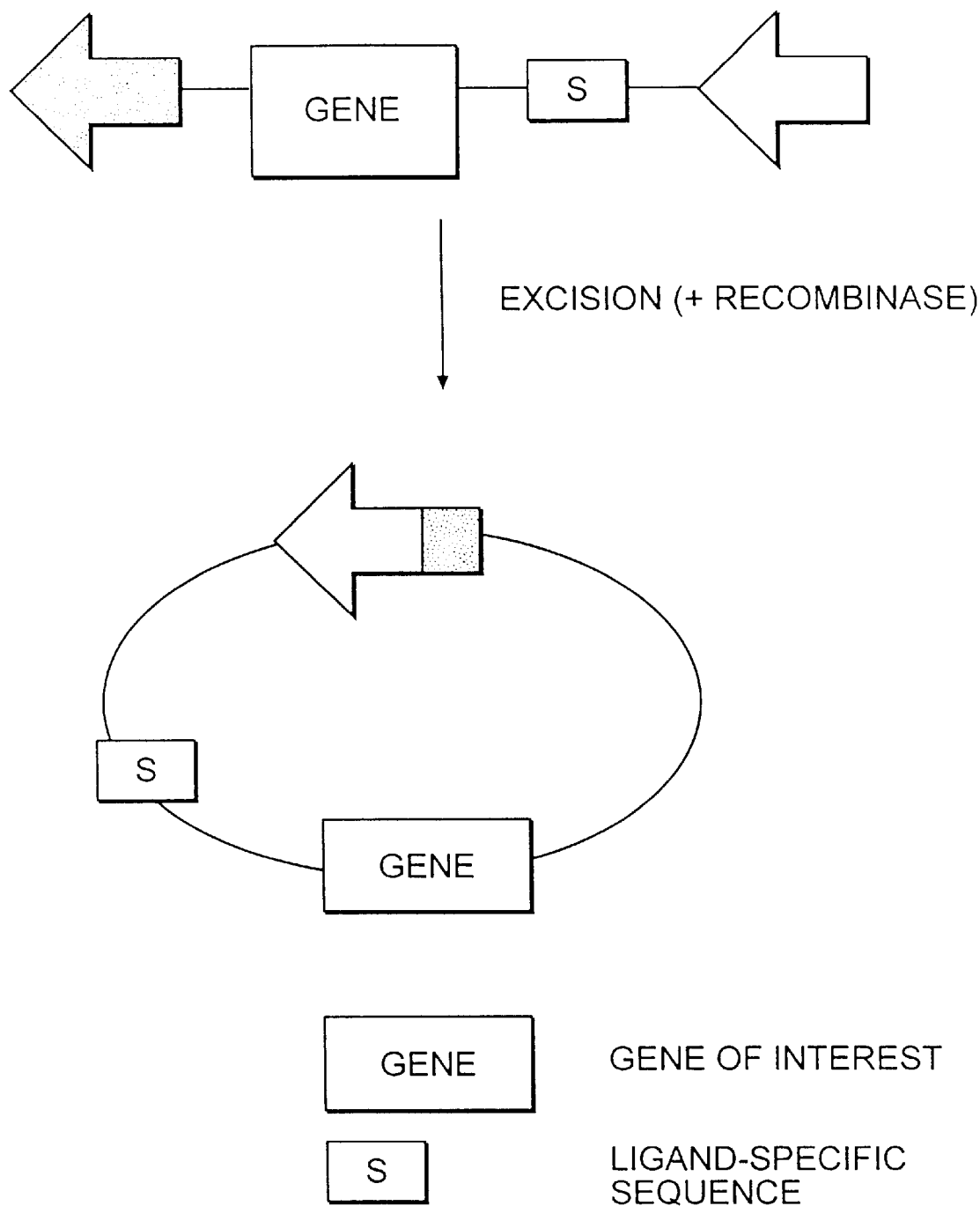
FIG. 3: Production of a minicircle containing a sequence specific to a ligand.

General techniques of cloning and molecular biology.

The standard methods of molecular biology, such as centrifugation of plasmid DNA in a cesium chloride-ethidium bromide gradient, digestion with restriction enzymes, gel electrophoresis, electroelution of DNA fragments from agarose gels, transformation in *E.coli*, precipitation of nucleic acids, and the like, are described in the literature (Maniatis et al., 1989, Ausubel et al., 1987). Nucleotide sequences were determined by the chain termination method according to the protocol already put forward (Ausubel et al., 1987).

Restriction enzymes were supplied by New-England Biolabs (Biolabs), Bethesda Research Laboratories (BRL) or Amersham Ltd. (Amersham).

To carry out ligation, DNA fragments are separated according to their size on 0.7 % agarose or 8% acrylamide gels, purified by electrophoresis and then electroelution, extracted with phenol, precipitated with ethanol and then incubated in a buffer comprising 50 mM Tris-HCl, pH 7.4, 10 mM MgCl$_2$, 10 mM, DTT, 2 mM ATP in the presence of phage T4 DNA ligase (Biolabs). Oligo-nucleotides are synthesized using phosphoramidite chemistry with the latter derivatives protected at the b position by a cyanoethyl group (Sinha et al., 1984, Giles 1985), with the Biosearch 8600 automatic DNA synthesizer, using the manufacturer's recommendations.

The ligated DNAs are used to transform the following strains rendered competent†: *E.coli* MC1060 [(LacIOPZYA)X74, galU, galK, strA$^r$, hsdR] (Casadaban et al., 1983); HB101 [hsdS20, supE44, recA13, ara-14, proA2, lacY1, galK2, rpsL20, xyl-5, mtl-1, λ–, F–] (Maniatis et al., 1989); and DH5α [endA1 hsdR17 supE44 thi-1 recA1 gyrA96 relA1 λ-Φ80 dlacZΔM15] for the plasmids.

LB and 2XTY culture media are used for the bacteriological part (Maniatis et al., 1989).

Plasmid DNAs are purified according to the alkaline lysis technique (Maniatis et al., 1989).

Definition of the terms employed and abbreviations.

Recombinant DNA: set of techniques which make it possible either to combine, within the same microorganism, DNA sequences which are not naturally combined, or to mutagenize a DNA fragment specifically.

ATP: adenosine 5'-triphosphate
BSA: bovine serum albumin
PBS: 10 mM phosphate buffer, 150 mM NaCl, pH 7.4
dNTP: 2'-deoxyribonucleoside 5'-triphosphates
DTT: dithiothreitol
kb: kilobases
bp: base pairs

EXAMPLE 1

Construction of a Plasmid Carrying the attP and attB Sequences of the Bacteriophage, in Repeated Direct Orientations.

The plasmid pNH16a was used as starting material, inasmuch as it already contains a fragment of bacteriophage λ carrying the attP sequence (Hasan and Szybalski, 1987). This plasmid was digested with EcoRI. Oligonucleotides which contain the attB sequence (Landy, 1989) were synthesized. They have the following sequence:

Oligonucleotide 5476 (SEQ ID No.1)
5'-AATTGTGAAGCCTGCTTTTTTATACTAAC TTGAGCGG-3'

Oligonucleotide 5477 (SEQ ID No.2)
5'-AATTCCGCTCAAGTTAGTATAAAAAAGCA GGCTTCAC-3'

They were hybridized to re-form the attB sequence and then ligated at the EcoRI site of the 4.2-kb EcoRI fragment of pNH16a (Hasan and Szybalski, 1987). After transformation of DH5α, a recombinant clone was retained. The plasmid thereby constructed was designated pXL2648 (see FIG. 4). This plasmid contains the attP and attB sequences of the bacteriophage in the direct orientation. Under the action of the integrase of the bacteriophage (Int protein), there should be excision of the sequences lying between the two att sites. This results in separation of the material inserted between the two att sequences from the origin of replication and from the resistance marker of the plasmid, which are positioned on the outside.

EXAMPLE 2

Obtaining a Minicircle in vivo in *E.coli*.

Figure 4:
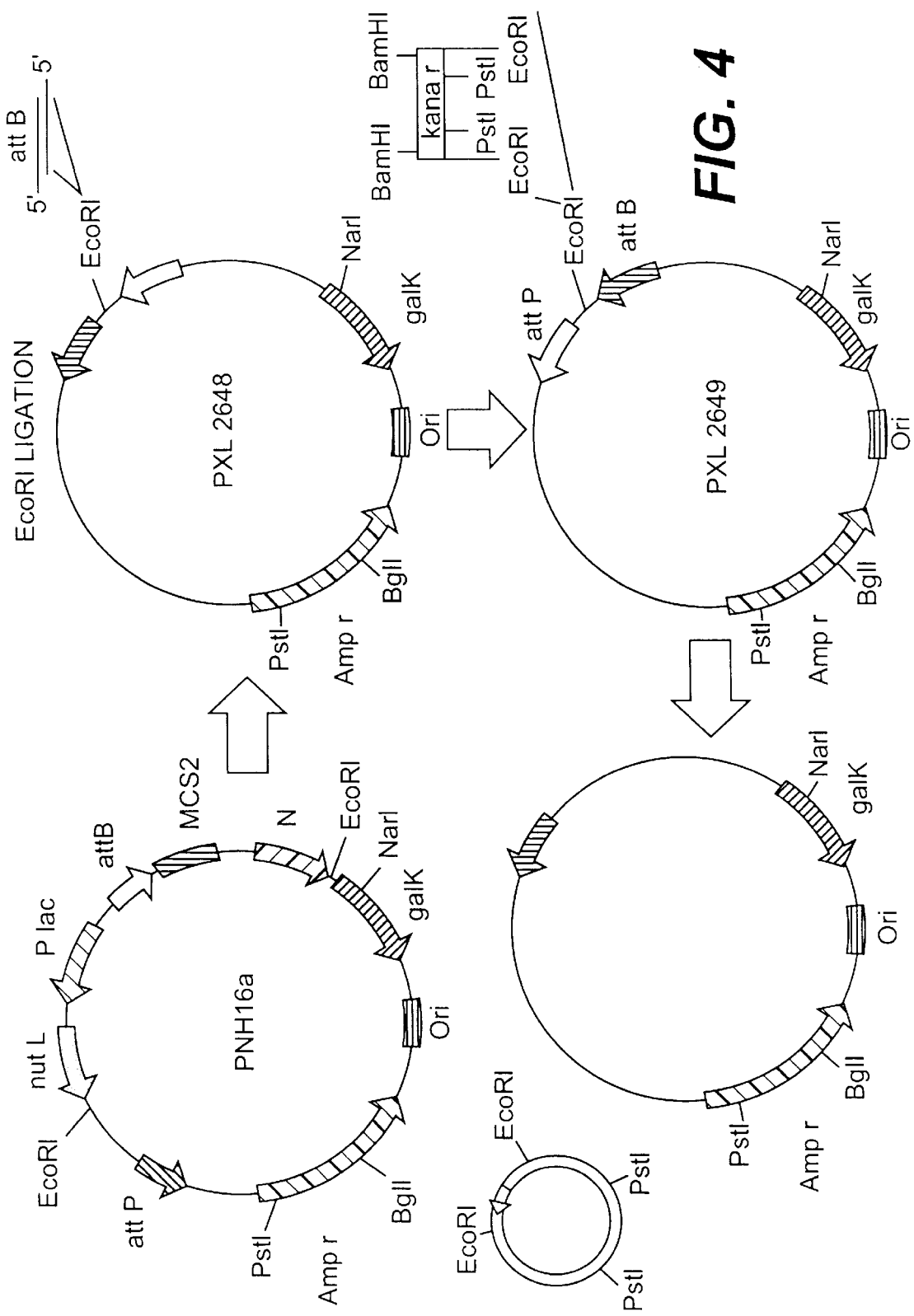
FIG. 4: Construction of pXL2649. Ori: Origin of replication; Kan$^r$: Marker gene conferring resistance to kanamycin; Amp$^r$: Marker gene conferring resistance to ampicillin; galK: Galactosidase gene of E.coli; Plac: Promoter of the lactose operon.

A cassette for resistance to kanamycin was cloned at the EcoRI site of plasmid pXL2648 (FIG. 4). This cassette originates from the plasmid pUC4KIXX (Pharmacia Biotech.). For this purpose, 10 µg of plasmid pUC4KIXX were digested with EcoRI and then separated by agarose gel electrophoresis; the 1.6-kb fragment containing the kanamycin resistance marker was purified by electro-elution; it was then ligated to plasmid pXL2648 linearized with EcoRI. The recombinant clones were selected after transformation into *E.coli* DH5α and selection for resistance to kanamycin. The expected restriction profile was observed on one clone; this plasmid clone was designated pXL2649 (FIG. 4). This plasmid was introduced by transformation into two *E.coli* strains:

D1210 [hsdS20, supE44, recA13, ara-14, proA2, lacY1, galK2, rpsL20, xyl-5, mtl-1, λ$^–$, F–, lacIg] (Sadler et al., 1980).

D1210HP, which corresponds to DH1210 lysogenized with the phage xis$^–$ (Xis$^–$ Kil$^–$) cI857 (Podjaska et al., 1985). The D1210HP strain [supE44 ara-14 galK2 Δ(gpt-proA)62 rpsL20 xy15 mtl1 recA13 Δ(mcrC-mrr) hsdS lacI$^q$] (λ[cI857 xis$^–$ ki1$^–$]), accession number I-2314, was deposited on Sep. 15, 1999 with the Collection National de Cultures de Microorganisms (CNCM), Institut Pasteur, 25 rue du Docteur Roux, F-75724 Paris Cédex 15, FRANCE.

The transformants were selected at 30° C. on 2XTY medium with kanamycin (50 mg/l). After reisolation on selective medium, the strains were inoculated into 5 ml of L medium supplemented with kanamycin (50 mg/l). After 16 h of incubation at 30° C. with agitation (5 cm of rotational amplitude), the cultures were diluted to 1/100 in 100 ml of the same medium. These cultures were incubated under the same conditions until an $OD_{610}$ of 0.3 was reached. At this point, half of the culture was removed and then incubated for 10 min at 42° C. to induce the lytic cycle of the phage, hence the expression of the integrase. After this incubation, the cultures were transferred again to 30° C. and then incubated for 1 h under these conditions. Next, culturing was stopped and minipreparations of plasmid DNA were produced. Irrespective of the conditions, in the strain D1210, the agarose gel electrophoresis profile of the undigested plasmid DNA of plasmid pXL2649 is unchanged, as is also the case in the strain D1210HP which has not been thermally induced. On the contrary, in D1210HP which has been incubated for 10 min at 42° C. and then cultured for 1 hour at 30° C., it is found that there is no longer a plasmid, but two circular DNA molecules: one of low molecular weight, migrating faster and containing an EcoRI site; and one of higher molecular weight, containing a unique BglI site, as expected. Hence there has indeed been excision of the sequences present between the two att sequences, and generation of a minicircle bereft of any origin of replication. This supercoiled circular DNA not carrying an origin of replication is termed a minicircle. This name takes, in effect, better account of the circular nature of the molecule. The starting plasmid pXL2649 is present, but it represents approximately 10% of the plasmid which has excised the sequences flanked by att.

The minicircle may then be purified by standard techniques of plasmid DNA purification, since it is supercoiled like plasmid DNA. These techniques comprise, inter alia, purification on a cesium chloride density gradient in the presence of ethidium bromide, or alternatively the use of anion exchange columns (Maniatis et al., 1989). In addition, if the plasmid DNA corresponding to the origin of replication and to the selectable marker is considered to be present in an excessively large amount, it is always possible, after purification, to use one or more restriction enzymes which will digest the plasmid and not the minicircle, enabling them to be separated by techniques that separate supercoiled DNA from linear DNA, such as in a cesium chloride density gradient in the presence of ethidium bromide (Maniatis et al., 1989).

EXAMPLE 3

Obtaining a Minicircle Containing a Cassette for the Expression of Luciferase.

In order to test the use of these minicircles in vivo, a reporter gene with the sequences required for its expression was cloned into plasmid pXL2649 (see Example 2). This was done using, more especially, a 3150-bp BqlII-BamHI cassette originating from pGL2-Control (Promega Biotech). This cassette contains the SV40 early promoter, the enhancer of the SV40 early promoter, the luciferase gene of *Photinus pyralis* and a polyadenylation site derived from SV40. The 3150-bp BglII-BamHI fragment was cloned at the BamHI site of pXL2649 digested with BamHI so as to replace the cassette for resistance to kanamycin by the cassette for the expression of luciferase from pGL2-control. The plasmid thus constructed was called pXL2650. In this plasmid, the attP and attB sites flank the cassette for the expression of luciferase. Site-specific recombination enables only the sequences required for the expression of luciferase together with the luciferase gene to be excised. This recombination may be carried out exactly as described in Example 2. A minicircle such as plasmid pXL2650 may be used thereafter in in vivo or in vitro transfection experiments.

A 1-liter culture of the strain D1210HP pXL2650 in 2XTY medium supplemented with ampicillin (50 mg/ml) was set up at 30° C. At an $OD_{610}$ equal to 0.3, the culture was transferred to 42° C. for 20 min, then replaced for 20 min at 30° C. The episomal DNA was prepared by the clear lysate technique (Maniatis et al., 1989), followed by a cesium chloride density gradient supplemented with ethidium bromide (Maniatis et al., 1989), then by an extraction of the ethidium bromide with isopropanol and by a dialysis. This DNA was shown to contain the minicircle. 100 μg of this preparation were digested with PstI, and the hydrolysate was then subjected to a cesium chloride density gradient supplemented with ethidium bromide (Maniatis et al., 1989). An identical result is obtained when the preparation is digested jointly with AlwNI and XmnI. The supercoiled form was recovered and, after removal of the ethidium bromide (Maniatis et al.), it was found to correspond only to the minicircle, lacking an origin of replication and any marker gene. This minicircle preparation may be used for in vitro and in vivo transfection experiments.

EXAMPLE 4

In vitro Transfection of Mammalian Cells, and More Especially of Human Cells, with a Minicircle.

The minicircle DNA containing the luciferase gene of *Photinus pyralis* as described in Example 3, that is to say corresponding to the minicircle generated from plasmid pXL2650, is diluted in 150 mM NaCl and mixed with a transfectant. It is possible to use various commercial transfectants, such as dioctadecylamidoglycylspermine (DOGS, Transfectam™, Promega), Lipofectin™ (Gibco-BRL), and the like, in different positive/negative charge ratios. By way of illustration, the transfecting agent was used in charge ratios greater than or equal to 3. The mixture is vortexed, left for 10 minutes at room temperature, diluted in culture medium without fetal calf serum, and then added to the cells in the proportion of 2 μg of DNA per culture well. The cells used are Caco-2, derived from a human colon adenocarcinoma, cultured according to a protocol described (Wils et al., 1994) and inoculated on the day before the experiment into 48-well culture plates in the proportion of 50,000 cells/well. After two hours at 37° C., 10% v/v of fetal calf serum is added and the cells are incubated for 24 hours at 37° C. in the presence of 5% $CO_2$. The cells are washed twice with PBS and the luciferase activity is measured according to the protocol described (such as the Promega kit). It is possible to use other lines (fibroblasts, lymphocytes, etc.) originating from different species, or alternatively cells taken from an individual (fibroblasts, keratinocytes, lymphocytes, etc.) and which will be reinjected into him or her after transfection.

EXAMPLE 5

In vitro Transfection of NIH 3T3 Cells.

The minicircle DNA containing the luciferase gene of *Photinus pyralis*, as described in Example 3, that is to say corresponding to the minicircle generated from plasmid pXL2650, was transfected in vitro into mammalian cells; pXL2650 and PGL2-Control (Promega Biotech.), which contain the same expression cassette, were used as control. The cells used are NIH 3T3 mouse fibroblasts, inoculated on the day before the experiment into 24-well culture plates in the proportion of 50,000 cells per well. The plasmid is diluted in 150 mM NaCl and mixed with the lipofectant RPR115335. However, it is possible to use various other commercial agents such as dioctadecylaminoglycylspermine (DOGS, Transfectam™, Promega) (Demeneix et al., Int. J. Dev. Biol. 35 (1991) 481), Lipofectin™ (Gibco-BRL)

Figure 5:
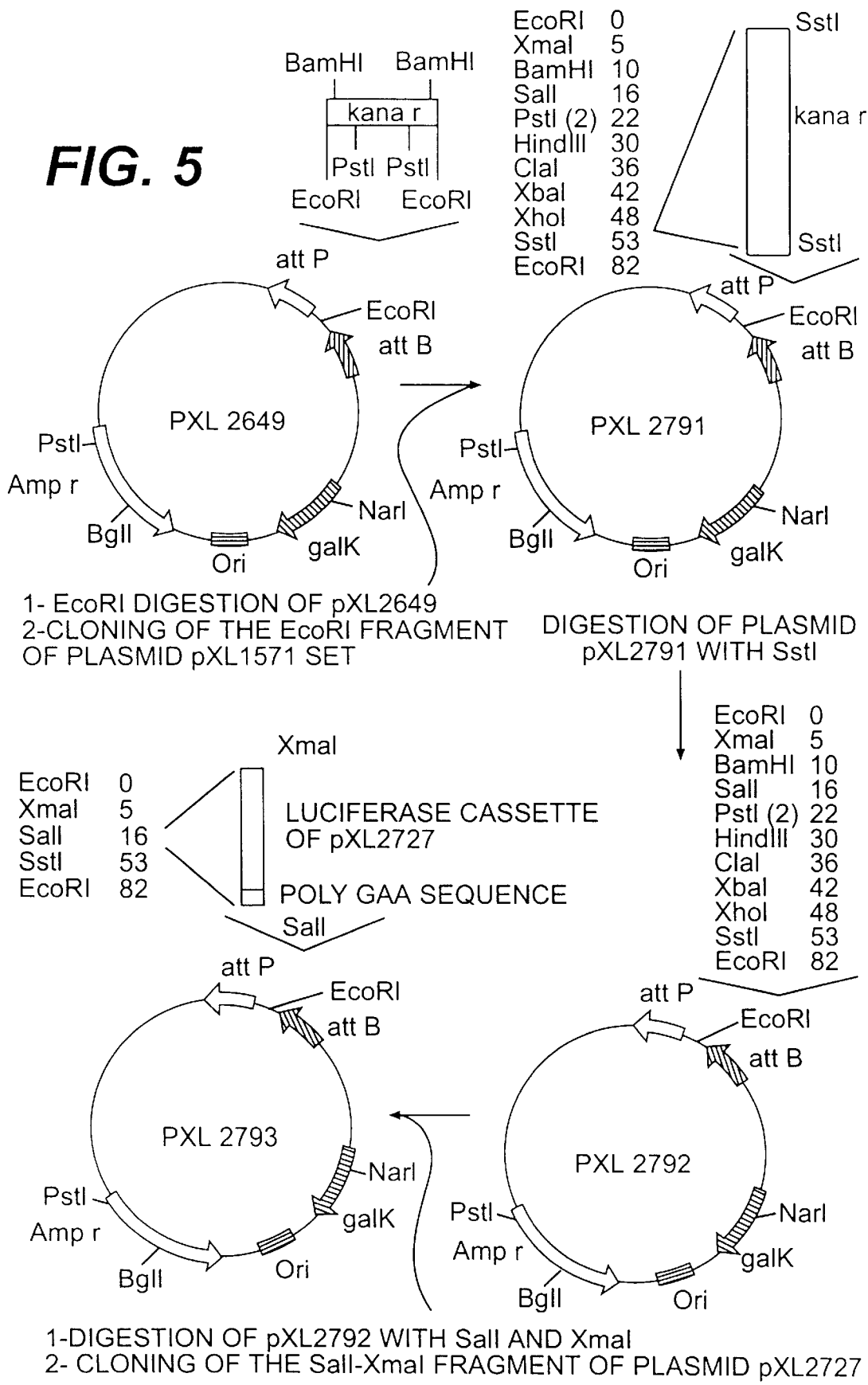
FIG. 5: Luciferase activity obtained after transfection of NIH3T3 mouse fibroblasts with plasmid pXL2650, the minicircle generated from plasmid pXL2650 and PGL2-Control (Promega, Biotech). The transfection was carried out under the following conditions: 0.5 mg of DNA per well, 50,000 cells per well. The lipofectant used is RPR 115335. The result is recorded in RLU per microgram of proteins as a function of the lipofectant/DNA charge ratio.
Figure 6:
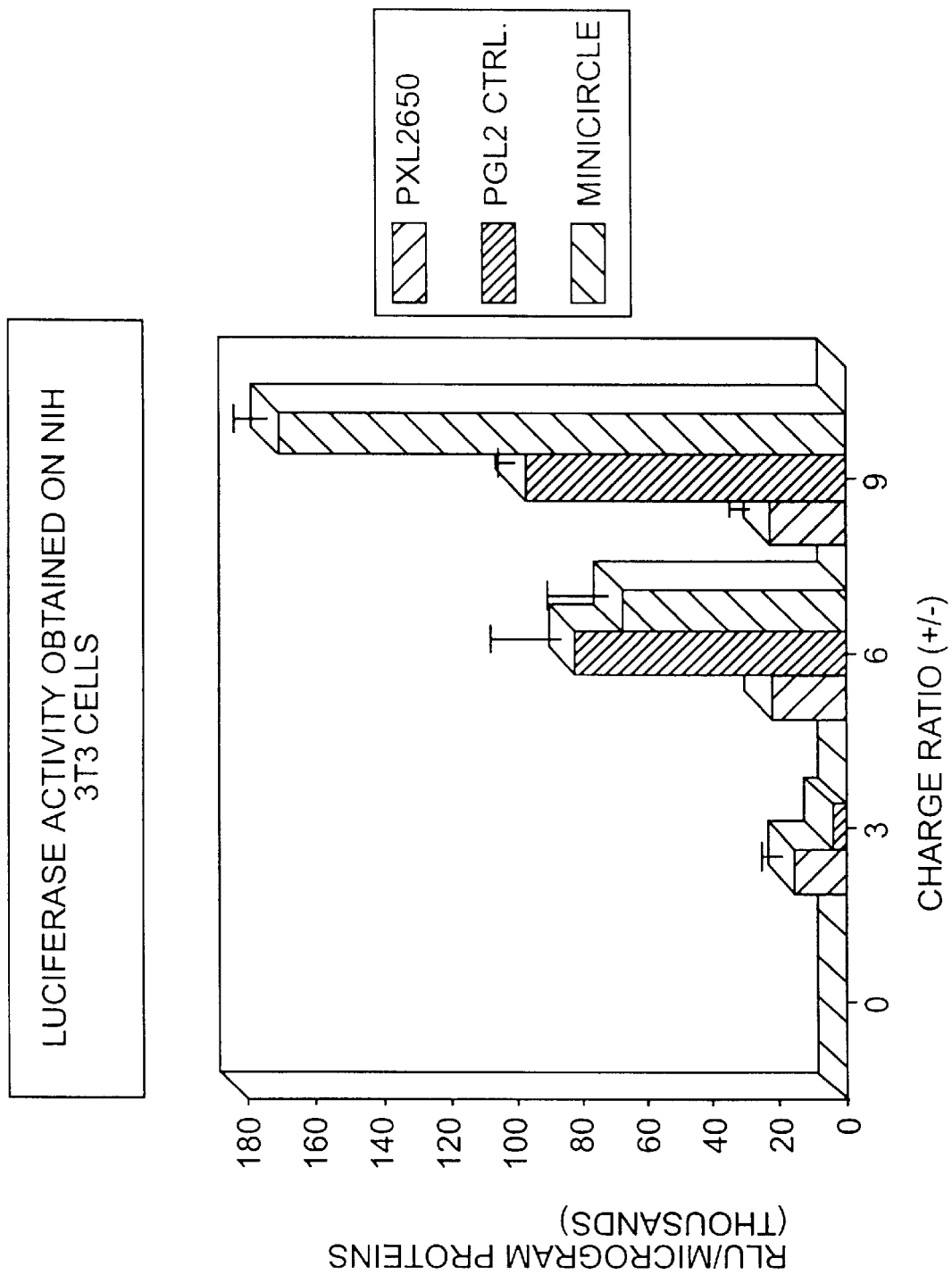
FIG. 6: Construction of the plasmid pXL2793. This plasmid generates, after recombination, a minicircle containing a synthetic homopurine-homopyrimidine sequence and the luciferase cassette of pXL2727.

(Fegner et al., Proc. Natl. Acad. Sci. USA 84 (1987) 7413), and the like. A positive charge of the lipofectant/negative charge of the DNA ratio equal to or greater than 3 is used. The mixture is vortexed, left for ten minutes at room temperature, diluted in medium without fetal calf serum, and then added to the cells in the proportion of 0.5 mg of DNA per culture well. After two hours at 37° C., 10% by volume of fetal calf serum is added and the cells are incubated for 48 hours at 37° C. in the presence of 5% $CO_2$. The cells are washed twice with PBS and the luciferase activity is measured according to the protocol described (Promega kit, Promega Corp. Madison, Wis.), on a Lumat LB9501 luminometer (EG and G Berthold, Evry). The transfection results corresponding to the conditions which have just been stated are presented in FIG. 5. They show unambiguously that the minicircle has the same transfection properties as plasmids possessing an origin of replication. Thus these minicircles could be used in the same way as standard plasmids in gene therapy applications.

EXAMPLE 6

Affinity Purification of a Minicircle Using a Triple-helix Interaction.

This example describes a method of purification of a minicircle according to the invention from a mixture containing the plasmid form which has excised it, by triple-helix type interactions which will take place with a synthetic DNA sequence carried by the minicircle to be purified. This example demonstrates how the technology of purification by triple-helix formation may be used to separate a minicircle from a plasmid form which has excised it.

6-1. Obtaining a Minicircle Containing a Synthetic Homopurine-homopyrimidine Sequence 6-1.1. Insertion of a homopurine-homopyrimidine sequence into plasmid pXL2650

Plasmid pXL2650 possesses a unique BamHI site immediately after the cassette containing the luciferase gene of *Photinus pyralis*. This unique site was used to clone the following two oligonucleotides:

4957 (SEQ ID No.3)
5'-GATCCGAAGAAGAAGAAGAAGAAGAAG AAGAAGAAGAAGAAGAAGAAGAAGAAC-3'

4958 (SEQ ID No.4)
5'-GATCGTTCTTCTTCTTCTTCTTCTTCT TCTTCTTCTTCTTCTTCTTCTTCG-3'

These oligonucleotides, when hybridized and cloned into plasmid pXL2650, introduce a homopurine-homopyrimidine sequence $(GAA)_{17}$, as described above.

To carry out this cloning, the oligonucleotides were first hybridized in the following manner. One µg of each of these two oligonucleotides were placed together in 40 ml of a final buffer comprising 50 mM Tris-HCl, pH 7.4, 10 mM $MgCl_2$. This mixture was heated to 95° C. and was then placed at room temperature so that the temperature would fall slowly. Ten ng of the mixture of hybridized oligonucleotides were ligated with 200 ng of plasmid pXL2650 linearized with BamHI, 30 ml of final. After ligation, an aliquot was transformed into DH5. The transformation mixtures were plated out on L medium supplemented with ampicillin (50 mg/l). Twenty-four clones were digested with PflMI and BamHI. One clone was found which had the size of the 950-bp PflMI-BamHI fragment increased by 50 bp. This clone was selected and designated pXL2651.

Plasmid pXL2651 was purified according to the Wizard Megaprep kit (Promega Corp., Madison, Wis.) according to the supplier's recommendations.

6-1.2. Insertion of a homopurine-homopyrimidine sequence into plasmid pXL2649 a) Insertion of new restriction sites on each side of the kanamycin cassette of pXL2649.

Plasmid pXL2649, as described in Example 2, was digested with EcoRI so as to take out the kanamycin cassette originating from plasmid pUC4KIXX (PharmaciaBiotech, Uppsala, Sweden). For this purpose, 5 mg of plasmid pXL2649 were digested with EcoRI. The 4.2-kb fragment was separated by agarose gel electrophoresis and purified by electroelution.

In addition, the plasmid pXL1571 was used. The latter was constructed from the plasmid pFR10 (Gene 25 (1983), 71–88), into which the 1.6-kb fragment originating from pUC4KIXX, corresponding to the kanamycin gene, was inserted at the SstI site. This cloning enabled 12 new restriction sites to be inserted on each side of the kanamycin gene.

Five micrograms of pXL1571 were dialysed with EcoRI. The 1.6-kb fragment corresponding to the kanamycin gene was separated by agarose gel electrophoresis and purified by electroelution. It was then ligated with the 4.2-kb EcoRI fragment of pXL2649. The recombinant clones were selected after transformation into *E. coli* DH5a and selection for resistance to kanamycin and to ampicillin. The expected restriction profile was observed on one clone; this plasmid clone was designated pXL2791.

b) Extraction of the kanamycin cassette from plasmid pXL2791

Plasmid pXL2791 was digested with SstI so as to take out the kanamycin cassette. The 4.2-kb fragment was separated by agarose gel electrophoresis and purified with the Jetsorb extraction gel kit (Genomed). It was then ligated. The recombinant clones were selected for resistance to ampicillin after transformation into *E. coli* DH5a. The expected restriction profile was observed on one clone. This plasmid clone was designated pXL2792. This clone comprises, inter alia, SalI and XmaI restriction sites between the attP and attB sites. c) Cloning of a homopurine-homopyrimidine sequence as well as of a cassette permitting the expression of luciferase between the two attP and attB sites of plasmid pXL2792

Plasmid pXL2727 was used. This plasmid, digested with XmaI and SalI, enables a fragment comprising the following to be taken out: the pCMV promoter, the luciferase gene of *Photinus pyralis*, a polyadenylation site derived from SV40 and a homopurine-homopyrimidine sequence. The latter was obtained after hybridization and cloning of the following two oligonucleotides:

6006: (SEQ ID No.16)
5'-GATCTGAAGAAGAAGAAGAAGAAGAAGA AGAAGAAGAAGAAGAAGAAGAAGAAGAAC TGCAGATCT-3'

6008: (SEQ ID No.17)
5'-GATCAGATCTGCAGTTCTTCTTCTTCTT CTTCTTCTTCTTCT TCTTCTTCTTCTTCTTCA-3'

The homopurine-homopyrimidine sequence present in pXL2727 was sequenced by the Sequenase Version 2.0 method (United States Biochemical Corporation). The result obtained shows that the homopurine-homopyrimidine sequence actually present in plasmid pXL2727 contains 10 repeats (GAA-CTT), and not 17 as the sequence of the oligonucleotides 6006 and 6008 suggested would be the case. The sequence actually present in plasmid pXL2727, read after sequencing on the strand corresponding to the oligonucleotide 6008, is as follows:

5'-GATCAGATCTGCAGTCTCTTCTTCTTCTT CTTCTTCTTCTTCT TCTTCTCTTCTCA-3' (SEQ ID No.18)

One microgram of pXL2727 was digested with XmaI and SalI. The 3.7-kb fragment was separated by agarose gel electrophoresis and purified with the Jetsorb extraction gel kit (Genomed). In addition, 1.7 mg of pXL2792 were digested with XmaI and SalI. The 4.2-kb fragment was separated on agarose gel, purified with the Jetsorb extraction gel kit (Genomed) and ligated with the 3.7-kb XmaI-SalI fragment of pXL2727. The recombinant clones were selected after transformation into E. coli DH5a and selection for resistance to ampicillin. The expected restriction profile was observed on one clone; this clone was designated pXL2793. Plasmid pXL2793 was purified using a caesium chloride density gradient according to a method already described (Maniatis et al., 1989).

6-2. Preparation of the Column Enabling Triple-helix Type Interactions with a Homopurine-homopyrimidine Sequence Present in the Minicircle to be Effected The column was prepared in the following manner:

The column used is a 1-ml HiTrap column activated with NHS (N-hydroxysuccinimide, Pharmacia), connected to a peristaltic pump (flow rate<1 ml/min). The specific oligonucleotide used possesses an $NH_2$ group at the 5' end.

For plasmid pXL2651, its sequence is as follows:

5'-GAGGCTTCTTCTTCTTCTTCTTCTT-3' (SEQ ID No.5)

For plasmid pXL2793, its sequence is as follows (oligo 116418):

5'-CTTCTTCTTCTTCTTCTTCTT-3' (SEQ ID No. 19)

The buffers used are the following:

Coupling buffer: 0.2 M $NaHCO_3$, 0.5 M NaCl, pH 8.3.
Washing buffer:
Buffer A: 0.5 M ethanolamine, 0.5 M NaCl, pH 8.3.
Buffer B: 0.1 M acetate, 0.5 M NaCl, pH 4.
Fixing and eluting buffer:
Buffer F: 2 M NaCl, 0.2 M acetate, pH 4.5.
Buffer E: 1 M Tris-HCl, pH 9, 0.5 mM EDTA.

The column is prepared in the following manner:

The column is washed with 6 ml of 1 mM HCl, and the oligonucleotide diluted in the coupling buffer (50 nmol in 1 ml) is then applied to the column and left for 30 minutes at room temperature. The column is washed with 3 ml of coupling buffer, then with 6 ml of buffer A, followed by 6 ml of buffer B. The latter two buffers are applied three times in succession to the column. In this way, the oligonucleotide is linked covalently to the column via a CONH link. The column is stored at 4° C. in PBS, 0.1% $NaN_3$.

6-3. Purification of a Minicircle Containing a Synthetic Homopurine-homopyrimidine Sequence, by a Triple-helix Type Interaction 6-3.1. Purification of plasmid pXL2651

Plasmid pXL2651 was introduced into the strain D1210HP. This recombinant strain [D1210HP (pXL2651)] was cultured as described in Example 3 so as to generate the minicircle containing the luciferase gene of Photinus pyralis. Twenty ml of culture were removed and centrifuged. The cell pellet is taken up in 1.5 ml of 50 mM glucose, 25 mM Tris-HCl, pH 8, 10 mM EDTA. Lysis is carried out with 2 ml of 0.2 M NaOH, 1% SDS, and neutralization with 1.5 ml of 3 M potassium acetate, pH 5. The DNA is then precipitated with 3 ml of 2-propranol, and the pellet is taken up in 0.5 ml of 0.2 M sodium acetate, pH 5, 0.1 M NaCl and loaded onto an oligonucleotide column capable of forming triple-helix type interactions with poly(GAA) sequences contained in the minicircle, as described above. After the column has been washed beforehand with 6 ml of buffer F, the solution containing the minicircle to be purified is incubated, after being applied to the column, for two hours at room temperature. The column is washed with 10 ml of buffer F and elution is then carried out with buffer E.

Purified DNA corresponding to the minicircle is thereby obtained. The minicircle obtained, analysed by agarose gel electrophoresis and ethidium bromide staining, takes the form of a single band of supercoiled circular DNA. Less than 5% of starting plasmid pXL2651 is left in the preparation.

6-3.2. Purification of plasmid pXL2793

The 7.9-kb plasmid pXL2793 was introduced into the strain D1210HP. This recombinant strain was cultured as described in Example 3, so as to generate the 4-kb minicircle containing the luciferase gene of Photinus pyralis and a 3.9-kb plasmid. Two hundred ml of culture were removed and centrifuged. The cell pellet was treated with the Wizard Megaprep kit (Promega Corp., Madison, Wis.) according to the supplier's recommendations. The DNA was taken up in a final volume of 2 ml of 1 mM Tris, 1 mM EDTA, pH 8. Two hundred and fifty microliters of this plasmid sample were diluted with buffer F in a final volume of 2.5 ml. The column was washed beforehand with 6 ml of buffer F. The whole of the diluted sample was loaded onto an oligonucleotide column capable of forming triple-helix type interactions with poly(GAA) sequences contained in the minicircle, prepared as described above. After washing with 10 ml of buffer F, elution is carried out with buffer E. The eluted sample is recovered in 1-ml fractions.

Figure 7:
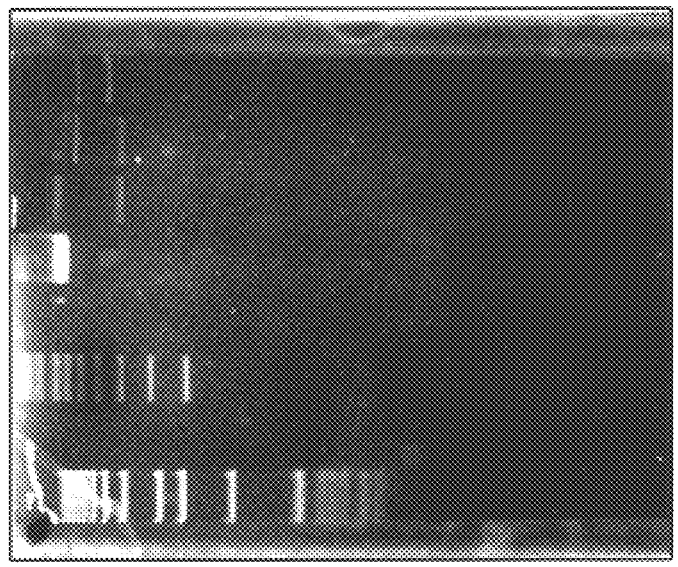
FIG. 7: Well 1 corresponds to the SalI digestion of the fraction eluted after purification with a triple-helix column. Well 2 corresponds to the XmnI digestion of the fraction eluted after purification with a triple-helix column. Well 3 corresponds to the undigested fraction eluted after purification with a triple-helix column. Well 4 corresponds to uninduced, undigested plasmid pXL2793. Wells 5 and 6 correspond, respectively, to the linear DNA and supercoiled DNA size markers.

By this method, purified DNA corresponding to the minicircle generated from pXL2793 is obtained. The DNA sample eluted from the column was analysed by agarose gel electrophoresis and ethidium bromide staining, and by enzyme restriction. For this purpose, the eluted fractions which were shown to contain DNA by assay at $OD_{260}$ nm were dialysed for 24 hours against 1 mM Tris, 1 mM EDTA, then precipitated with isopropanol and taken up in 200 ml of $H_2O$. Fifteen microliters of the sample thereby obtained were digested with SalI, this restriction site being present in the minicircle and not in the 3.9-kb plasmid generated by the recombination, or with XmnI, this restriction site being present in the 3.9-kb plasmid generated by the recombination and not in the minicircle. The result obtained is presented in FIG. 7, showing that the minicircle has been purified of the recombinant plasmid.

EXAMPLE 7

In vivo Transfection of Mammalian Cells with a Minicircle

This example describes the transfer of a minicircle coding for the luciferase gene into the brain of newborn mice. The minicircle (30 μg) is diluted in sterile 150 mM NaCl to a concentration of 1 μg/μl. A synthetic transfectant such as dioctadecylamidoglycylspermine (DOGS) is then added in a positive/negative charge ratio less than or equal to 2. The mixture is vortexed, and 2 μg of DNA are injected into the cerebral cortex of anaesthetized newborn mice using a micromanipulator and a microsyringe. The brains are removed 48 hours later, homogenized and centrifuged and the supernatant is used for the assay of luciferase by the protocols described (such as the Promega kit).

EXAMPLE 8

Use of the par Locus of RK2 to Reduce the Presence of Minicircle or Miniplasmid Topoisomers This example demonstrates the presence of topological forms derived i) from the plasmid possessing the attP and attB sequences in the direct orientation, ii) from the minicircle or iii) from the miniplasmid, after the action of the integrase of bacteriophage 1 in *E. coli*. This example also shows that these topological or oligomeric forms may be resolved by using the par locus of RK2 (Gerlitz et al., 1990 J. Bacteriol. 172 p. 6194). In effect, this locus contains, in particular, the parA gene coding for a resolvase acting at the mrs (multimer resolution system) site (Eberl et al., 1994 Mol. Microbiol. 12 p. 131).

8-1. Construction of Plasmids pXL2777 and pXL2960

Plasmids pXL2777 and pXL2960 are derived from the vector pXL2776, and possess in common the minimal replicon of ColE1, the gene of the transposon Tn5 coding for resistance to kanamycin and the attP and attB sequences of bacteriophage 1 in the direct orientation. These plasmids differ in respect of the genes inserted between the attP and attB sequences, in particular pXL2777 contains the omegon cassette (coding for the gene for resistance to spectinomycin) whereas plasmid pXL2960 carries par locus of RK2.

8-1.1. Minimal vector pXL2658

The vector pXL2658 (2.513 kb) possesses the minimal replicon of ColE1 originating from pBluescript (ori) and the gene of the transposon Tn5 coding for resistance to kanamycin (Km) as selectable marker. After the BsaI end has been blunted by the action of the Klenow enzyme, the 1.15-kb BsaI-PvuII fragment of pBKS+ (obtained from Stratagene) was cloned with the 1.2-kb SmaI fragment of pUC4KIXX (obtained from Pharmacia) to generate the plasmid pXL2647. The oligo-nucleotides 5542 5'(AGC TTC TCG AGC TGC AGG ATA TCG AAT TCG GAT CCT CTA GAG CGG CCG CGA GCT CC)3' (SEQ ID No.20) and 5543 5'(AGC TGG AGC TCG CGG CCG CTC TAG AGG ATC CGA ATT CGA TAT CCT GCA GCT CGA GA)3' (SEQ ID No.21) were hybridized with one another and then cloned at the HindIII site of pXL2647; in this way pXL2658 is constructed. In this plasmid, the multiple cloning site is SstI, NotI, XbaI, BamHI, EcoRI, EcoRV, PstI, XhoI and HindIII between the origin of replication and the gene coding for resistance to kanamycin.

8-1.2. Vector pXL2776 containing the attP and attB sequences of phage 1

Figure 8:
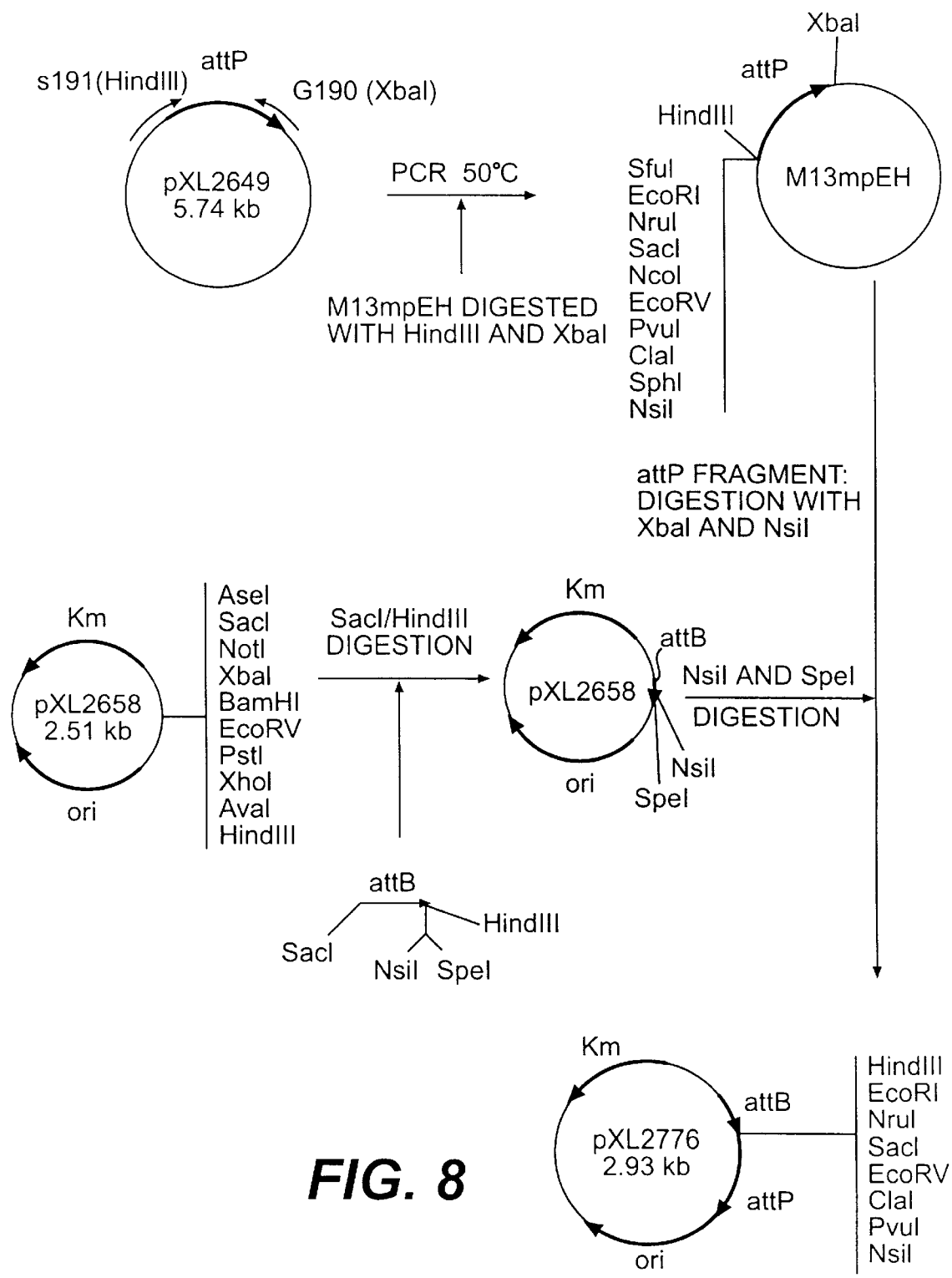
FIG. 8: Diagrammatic description of the construction of the plasmid pXL2776.

The vector pXL2776 (2.93 kb) possesses the minimal replicon of ColE1 originating from pBluescript, the gene coding for resistance to kanamycin and the attP and attB sequences of bacteriophage 1 in the direct orientation, see FIG. 8. The 29-bp attB sequence (Mizuuchi et al., 1980 Proc. Natl. Acad. Sci. USA 77 p. 3220) was introduced between the SacI and HindIII restriction sites of pXL2658 after the sense oligonucleotide 6194 5'(ACT AGT GGC CAT GCA TCC GCT CAA GTT AGT ATA AAA AAG CAG GCT TCA G)3' (SEQ ID No.22) has been hybridized with the antisense oligonucleotide 6195 5'(AGC TCT GAA GCC TGC TTT TTT ATA CTA ACT TGA GCG GAT GCA TGG CCA CTA GTA GCT)3' (SEQ ID No.23) in such a way that the SacI and HindIII sites are no longer re-formed after cloning. This plasmid, the sequence of which was verified with respect to attB, is then digested with SpeI and NsiI in order to introduce in it the attP sequence flanked by the NsiI and XbaI restriction sites and thus to generate plasmid pXL2776. The attP sequence was obtained by PCR amplification using plasmid pXL2649 (described in Example 2) as template, the sense oligonucleotide 6190 5'(GCG TCT AGA ACA GTA TCG TGA TGA CAG AG)3' (SEQ ID No.24) and the antisense oligonucleotide 6191 5'(GCC AAG CTT AGC TTT GCA CTG GAT TGC GA)3' (SEQ ID No.25), and performing 30 cycles during which the hybridization temperature is 50° C. The PCR product digested at the XbaI and HindIII sites was cloned into the phage M13mpEH between the XbaI and HindIII sites. The amplified sequence is identical to the attP sequence described in Lambda II (edited by R. W. Hendrix, J. W. Roberts, F. W. Stahl, R. A. Weisberg; Cold Spring Harbor Laboratory 1983) between positions 27480 and 27863.

8-1.3. Plasmid pXL2777

Plasmid pXL2777 (6.9 kb) possesses the minimal replicon of ColE1 originating from pBluescript, the gene coding for resistance to kanamycin, the attP and attB sequences of bacteriophage 1 in the direct orientation and separated by the sacB gene coding for levansucrase of *B. subtilis* (P. Gay et al., 1983 J. Bacteriol. 153 p. 1424), and the Sp omegon coding for the gene for resistance to spectinomycin Sp and streptomycin Sm (P. Prentki et al., 1984 Gene 29 p. 303). The sacB-Sp cassette having EcoRV and NsiI cloning ends comes from the plasmid pXL2757 (FR95/01632) and was cloned between the EcoRV and NsiI sites of pXL2776 to form pXL2777.

8-1.4. Plasmid pXL2960

Plasmid pXL2960 (7.3 kb) possesses the minimal replicon of ColE1 originating from pBluescript, the gene coding for resistance to kanamycin and the attP and attB sequences of bacteriophage 1 in the direct orientation and separated by i) the sacB gene coding for levansucrase of *B. subtilis* (P. Gay et al., 1983 J. Bacteriol. 153 p. 1424) and ii) the par locus of RK2 (Gerlitz et al., 1990 J. Bacteriol. 172 p. 6194). The par cassette having BamHI ends comes from the plasmid pXL2433 (PCT/FR95/01178) and was introduced between the BamHI sites of pXL2777 to generate pXL2960.

8-2. Resolution of Minicircle or Miniplasmid Topoisomers

Figure 9:
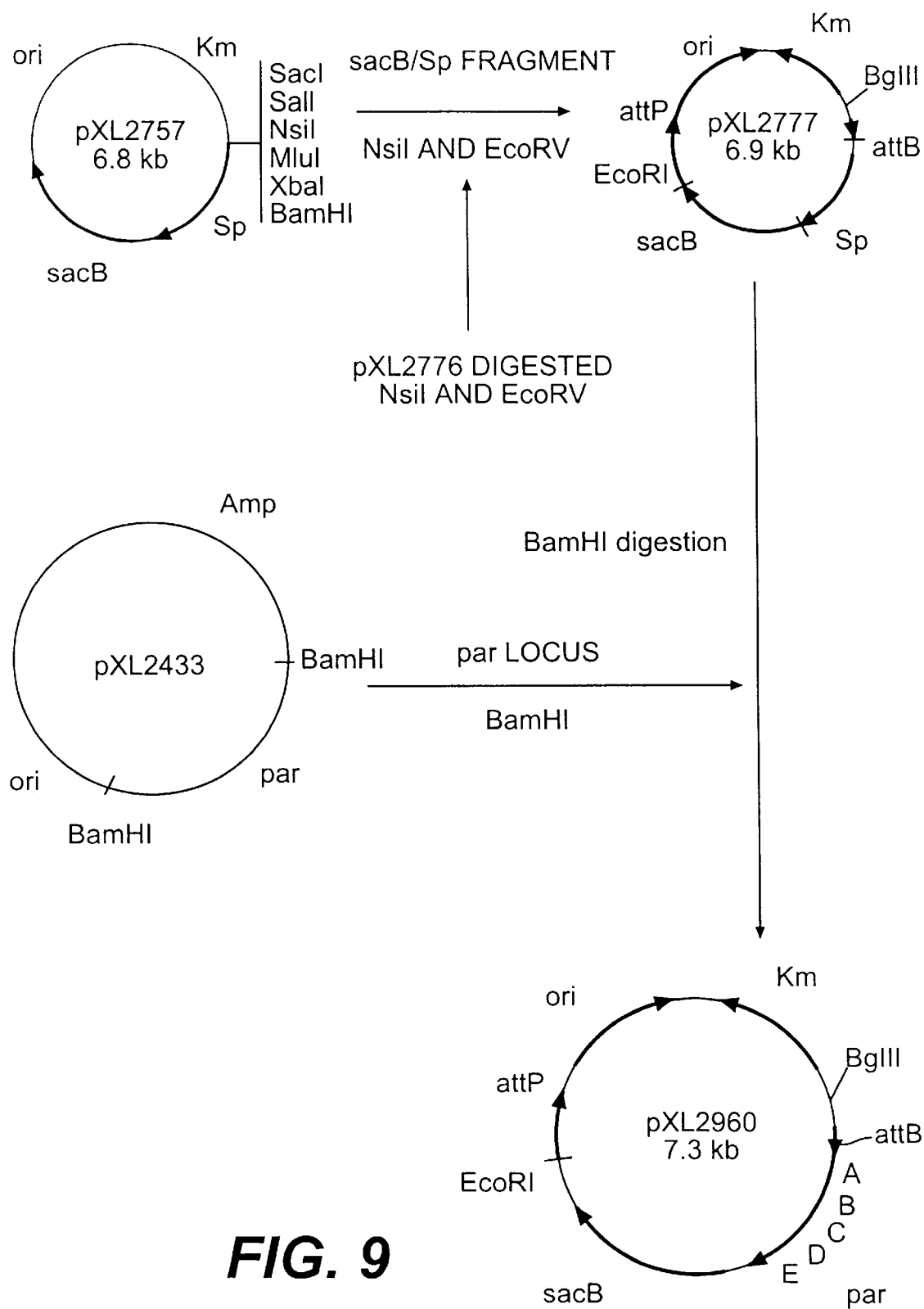
FIG. 9: Diagrammatic description of the constructions of the plasmids pXL2777 and pXL2960.
Figure 10:
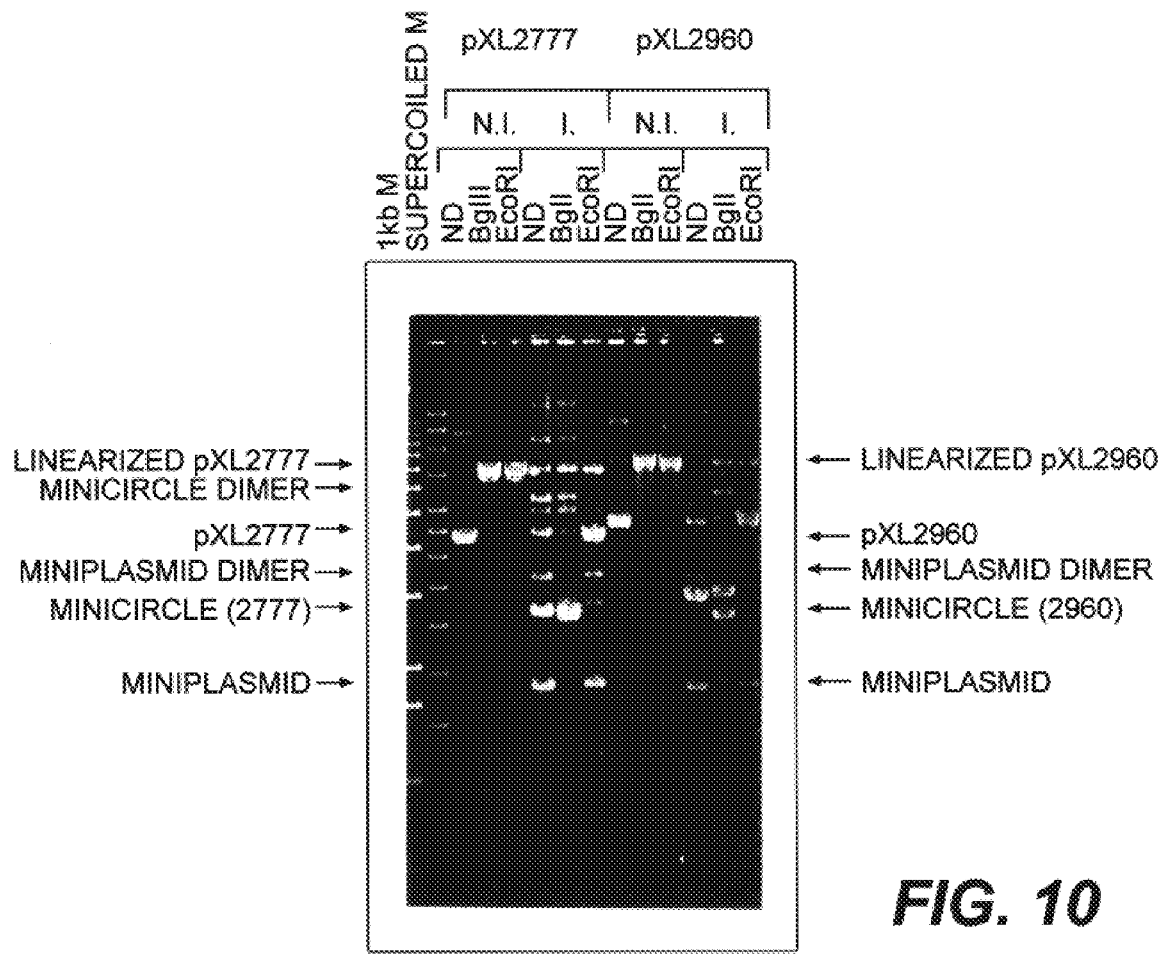
FIG. 10: Action of the integrase of bacteriophage 1 in *E. coli* on plasmids pXL2777 and pXL2960. M: linear DNA or supercoiled DNA 1 kb molecular weight marker. N.I.: not induced. I: induced. N.D.: not digested.
Figure 11:
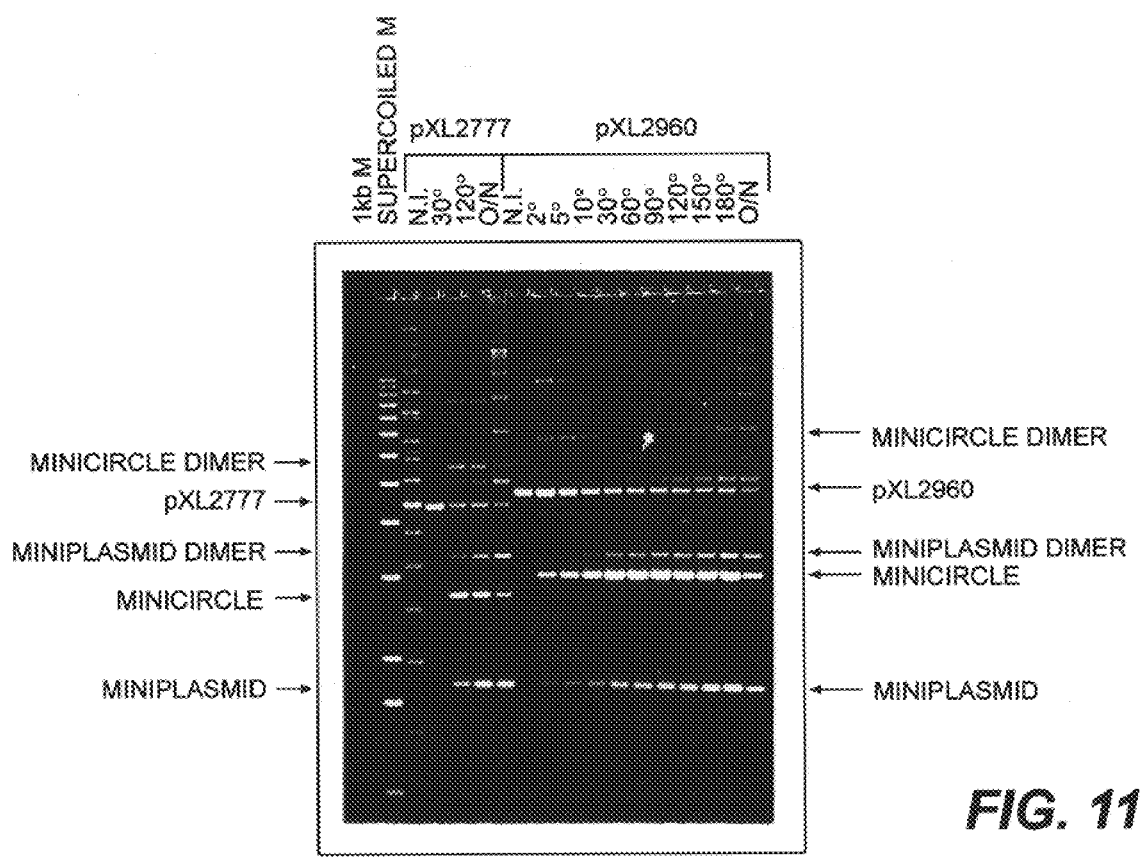
FIG. 11: Kinetics of recombination of the integrase of bacteriophage 1 in *E. coli* on plasmids pXL2777 and pXL2960. 2': 2 minutes. O/N: 14 hours. M: linear DNA or supercoiled DNA 1 kg molecular weight marker. N.I.: not induced. I: induced. N.D.: not digested.

Plasmids pXL2777 and pXL2960 were introduced by transformation into *E. coli* strain D1210HP. The transformants were selected and analysed as described in Example 2, with the following modifications: the expression of the integrase was induced at 42° C. for 15 min when the optical density of the cells at 610 nm is 1.8, and the cells are then incubated at 30° C. for 30 min, see FIG. 9, or for a period varying from 2 minutes to 14 hours (O/N), see FIG. 10. The plasmid DNA originating from uninduced and induced cultures was then analysed on agarose gel before or after digestion with a restriction enzyme exclusive to the minicircle portion (EcoRI) or miniplasmid portion (BglII), see Figure Y, or after the action of DNA topoisomerase A or the gyrase of *E. coli*. The supercoiled dimer forms of minicircle or miniplasmid are clearly revealed by i) their molecular weight, ii) their linearization by the restriction enzyme, iii) their change in topology through the action of topoisomerase A (relaxed dimer) or of the gyrase (supersupercoiled dimer), iv) specific hybridization with an internal fragment peculiar to the minicircle or the miniplasmid. Other topological forms of higher molecular weights than that of the initial plasmid originate from the initial plasmid or the minicircle or the miniplasmid, since they disappear after digestion with the restriction enzyme exclusive to the minicircle portion (EcoRI) or miniplasmid portion (BglII). These forms are much less abundant with pXL2960 than with pXL2777 as initial plasmid, see FIG. 10. In particular, the dimer form of minicircle is present to a not insignificant extent with plasmid pXL2777, whereas it is invisible with plasmid pXL2960 when the cells are incubated for at least 30 min at 30° C., see FIGS. 9 and 10. It should be noted that minicircle dimers are observed at the beginning of the kinetic experiment with pXL2960 (2 to 10 min), and are thereafter resolved (after 30 min), see FIG. 10. Consequently, the par locus leads to a significant reduction in the oligomeric/topological forms resulting from the action of the integrase of bacteriophage 1 in *E. coli* on plasmids containing the attP and attB sequences in the direct orientation.

IDENTIFICATION OF THE NUCLEOTIDE SEQUENCES

SEQ ID No.1: oligonucleotide 5476:
5'-AATTGTGAAGCCTGCTTTTTTATACTAACTTGAGCGG-3'

SEQ ID No.2: oligonucleotide 5477
5'-AATTCCGCTCAAGTTAGTATAAAAAAGCAGGCTTCAC-3'

SEQ ID No.3: oligonucleotide 4957:
5'-GATCCGAAGAGAGAAGAAGAAGAAGAAGAAGAAGAAGAAGAAGAAGAAGAAGAAC-3'

SEQ ID No.4: oligonucleotide 4958:
5'-GATCGTTCTTCTTCTTCTTCTTCTTCTTCTTCTTCTTCTTCTTCTTCTTCTTCG-3'

SEQ ID No.5: oligonucleotide poly-CTT:
5'-GAGGCTTCTTCTTCTTCTTCTTCTT-3'

SEQ ID No.6: (attB sequence of phage lambda):
5'-CTGCTTTTTTATACTAACTTG-3'

SEQ ID No.7: (attP sequence of phage lambda):
5'-CAGCTTTTTTATACTAAGTTG-3'

SEQ ID No.8: (attB sequence of phage P22):
5'-CAGCGCATTCGTAATGCGAAG-3'

SEQ ID No.9: (attP sequence of phage P22):
5'-CTTATAATTCGTAATGCGAAG-3'

SEQ ID No.10: (attB sequence of phage F80):
5'-AACACTTTCTTAAATGGTT-3'

SEQ ID No.11: (attP sequence of phage F80):
5'-AACACTTTCTTAAATTGTC-3'

SEQ ID No.12: (attB sequence of phage HP1):
5'-AAGGGATTTAAAATCCCTC-3'

SEQ ID No.13: (attP sequence of phage HP1):
5'-ATGGTATTTAAAATCCCTC-3'

SEQ ID No.14: (att sequence of plasmid pSAM2):
5'-TTCTCTGTCGGGGTGGCGGGATTTGAACCCACGACCTCTTCGTCCCGAA-3'

SEQ ID No.15: (Recognition sequence of the resolvase of the transposon Tn3):
5'-CGTCGAAATATTATAAATTATCAGACA-3'

SEQ ID No.16: oligonucleotide 6006:
5'-GATCTGAAGAAGAAGAAGAAGAAGAAGAAGAAGAAGAAGAAGAAGAACTGCAGATCT-3'

SEQ ID No.17: oligonucleotide 6008:
5'-GATCAGATCTGCAGTTCTTCTTCTTCTTCTTCTTCTTCTTCTTCTTCTTCTTCTTCTTCA-3'

SEQ ID No.18: (Sequence present in plasmid pXL2727 corresponding to the oligonucleotide 6008):
5'-GATCAGATCTGCAGTCTCTTCTTCTTCTTCTTCTTCTTCTTCTTCTTCTCTTCTTCA-3'

SEQ ID No.19: (oligonucleotide 116418):
5'-CTTCTTCTTCTTCTTCTTCTT-3'

SEQ ID No.20: (oligonucleotide 5542):
5'-AGCTTCTCGAGCTGCAGGATATCGAATTCGGATCCTCTAGAGCGGCCGCGAGCTCC-3'

SEQ ID No.21: (oligonucleotide 5543):
5'-AGCTGGAGCTCGCGGCCGCTCTAGAGGATCCGAATTCGATATCCTGCAGCTCGAGA-3'

SEQ ID No.22: sense oligonucleotide 6194:
5'-ACTAGTGGCCATGCATCCGCTCAAGTTAGTATAAAAAAGCAGGCTTCAG-3'

SEQ ID No.23: antisense oligonucleotide 6195:
5'-AGCTCTGAAGCCTGCTTTTTTATACTAACTTGAGCGGATGCATGGCCACTAGTAGCT-3'

SEQ ID No.24: sense oligonucleotide 6190:
5'-GCGTCTAGAACAGTATCGTGATGACAGAG-3'

SEQ ID No.25: antisense oligonucleotide 6191:
5'-GCCAAGCTTAGCTTTGCACTGGATTGCGA-3'

Bibliographic References

Ausubel et al. Current protocols in molecular biology 1987–1988. John Willey and Sons, New York.
Behr J. P. 1993. Acc. Chem. Res. 26:274–278.
Casadaban et al. 1983. Methods Enzymol. 100, 293–308.
Cotten et al. E. 1993. Curr. Biol. 4:705–710.
Giles, J. W. 1985. Am. Biotechnol., November/December.
Hasan et al. 1987. Gene 56:145–151.
Jain, R. K. 1987. Cancer Res. 47:3039–3051.
Landford et al. 1986. Cell 46:575–582.
Landy, A. 1989. Ann. Rev. Biochem. 58:913–949.
Maniatis, T., E. F. Fritsch, and J. Sambrook. 1989. Molecular cloning: a laboratory manual, second edition. Cold Spring Harbor Laboratory, Cold Spring Harbor Laboratory Press, New York.
Nabel et al. 1992. Human Gene Therapy 3:399–410.
Podhajska et al. 1985. Gene 40:163:168.
Sadler et al. 1980. Gene, 8:279–300.
Sinha et al. 1984. Acids Res., 12, 4539–4557.
Stark et al. 1992. Trends Genet. 8:432–439.
Viera et al. 1982. Gene, 19, 259–268.
Wils et al. Biochem. Pharmacol. 48:1528–1530.

What is claimed is:

1. A double-stranded DNA molecule, comprising an expression cassette containing a gene of interest under control of a transcription promoter and a transcription terminator active in a mammalian cell, wherein said molecule:
   is in circular and supercoiled form,
   lacks an origin of replication,
   lacks a marker gene, and
   comprises a region resulting from site-specific recombination between two sequences, said region being located outside the expression cassette.

2. The molecule according to claim 1, further comprising a sequence which interacts specifically with an oligonucleotide to form a triple helix by hybridization.

3. The molecule according to claim 2, wherein the sequence which forms a triple helix comprises from 5 to 30 base pairs.

4. The molecule according to claim 2, wherein the sequence which forms a triple helix is a homopurine-homopyrimidine sequence.

5. The molecule according to claim 1, wherein said region results from site-specific recombination between two att attachment sequences, two recognition sequences of a resolvase of a transposon, or two mrs sequences of plasmid RK2.

6. The molecule according to claim 1, further comprising an mrs sequence originating from a par locus of RK2.

7. The molecule according to claim 1, wherein the gene of interest is a nucleic acid coding for a therapeutic, vaccine, agricultural, or veterinary product.

8. The molecule according to claim 1, wherein said molecule is obtained by excision from a plasmid or chromosome by site-specific recombination.

9. A recombinant DNA comprising a polynucleotide comprising an expression cassette positioned between two sequences positioned in direct orientation, which recombine by site-specific recombination in the presence of a recombinase, wherein said expression cassette comprises a gene of interest under control of a transcription promoter and a transcription terminator active in a mammalian cell, and wherein said polynucleotide lacks an origin of replication and a marker gene.

10. The recombinant DNA according to claim 9 further comprising an origin of replication and, optionally, a marker gene, wherein the origin of replication and optional marker gene are located outside said polynucleotide.

11. The recombinant DNA according to claim 9, wherein the recombinase is a recombinase of an integrase family of phage lambda or of a resolvase family of transposon Tn3.

12. The recombinant DNA according to claim 9, wherein the two sequences which recombine by site-specific recombination are derived from a bacteriophage.

13. The recombinant DNA according to claim 12, wherein the two sequences which recombine by site-specific recombination consist of att attachment sequences of a bacteriophage or sequences derived therefrom.

14. The recombinant DNA according to claim 13, wherein the two sequences which recombine by site-specific recombination consist of attachment sequences of bacteriophage lambda, P22, Φ080, P1, or HP1, of plasmid pSAM2, or of sequences derived therefrom.

15. The recombinant DNA according to claim 14, wherein the sequences which recombine by site-specific recombination comprise all or part of SEQ ID Nos. 1, 2, 6, 7, 8, 9, 10, 11, 12, 13, or 14.

16. The recombinant DNA according to claim 12, wherein the two sequences which recombine by site-specific recombination are derived from bacteriophage P1.

17. A plasmid comprising:
   a) a bacterial origin of replication and optionally, a marker gene; and
   b) a polynucleotide comprising an expression cassette positioned between attP and attB sequences of a bacteriophage lambda, P22, Φ80, P1, or HP1, or of plasmid pSAM2, positioned in direct orientation, which recombine by site-specific recombination in the presence of a recombinase, wherein said expression cassette comprises a gene of interest under control of a transcription promoter and a transcription terminator active in a mammalian cell, and wherein said polynucleotide lacks an origin of replication and a marker gene.

18. The plasmid according to claim 17, wherein the attP and attB sequences which recombine by site-specific recombination are attachment sequences of bacteriophage lambda.

19. A plasmid comprising:
   a) a bacterial origin of replication and optionally, a marker gene; and
   b) a polynucleotide comprising an expression cassette positioned between two inverted repeat sequences of bacteriophage P1 (loxP region) positioned in direct orientation, which recombine by site specific recombination in the presence of a recombinase; wherein the expression cassette comprises a gene of interest under control of a transcription promoter and a transcription terminator active in a mammalian cell, and wherein the polynucleotide lacks an origin of replication and a marker gene.

20. The recombinant DNA according to claim 9, wherein the two sequences which recombine by site-specific recombination are derived from a transposon.

21. The recombinant DNA according to claim 20, wherein the two sequences which recombine by site-specific recombination consist of recognition sequences of a resolvase of a transposon Tn3, Tn21, or Tn522, or sequences derived therefrom.

22. The recombinant DNA according to claim 21, wherein the two sequences which recombine by site-specific recombination comprise all or part of sequence SEQ ID No.15.

23. The recombinant DNA according to claim 9, wherein the two sequences which recombine by site-specific recombination are derived from a par region of plasmid RP4.

24. The recombinant DNA according to claim 9, wherein the expression cassette further comprises a sequence which interacts specifically with an oligonucleotide to form a triple helix by hybridization.

25. A plasmid comprising:
   a) an origin of replication and optionally, a marker gene; and
   b) a polynucleotide comprising at least one gene of interest and a sequence which interacts specifically with an oligonucleotide to form a triple helix by hybridization, wherein the at least one gene of interest and the oligonucleotide interacting sequence are positioned between two sequences positioned in direct orientation, which recombine by site-specific recombination in the presence of a recombinase, and wherein the polynucleotide lacks an origin of replication and a marker gene.

26. A plasmid comprising:
   a) an origin of replication and optionally, a marker gene; and
   b) a polynucleotide comprising at least one gene of interest and an mrs sequence originating from a par locus of plasmid RK2, wherein the at least one gene of interest and the mrs sequence are positioned between two sequences positioned in direct orientation, which recombine by site-specific recombination in the presence of a recombinase, and wherein the polynucleotide lacks an origin of replication and a marker gene.

27. The plasmid according to claim 26, wherein the polynucleotide further comprises a sequence which interacts specifically with an oligonucleotide to form a triple helix by hybridization, wherein the oligonucleotide interacting sequence is placed between the two sequences positioned in direct orientation, which recombine by site-specific recombination.

28. A plasmid comprising:
   a) an origin of replication and optionally, a marker gene; and
   b) a polynucleotide comprising:
      1) a first set of two sequences positioned in direct orientation, which recombine by integrase-dependent site-specific recombination;
      2) a second set of two sequences positioned in direct orientation, which recombine by resolvase-dependent site-specific recombination;
      3) at least one gene of interest; and,
      4) optionally, a sequence which interacts specifically with an oligonucleotide to form a triple helix by hybridization,
wherein each integrase-dependent sequence of 1) is positioned next to a resolvase-dependent sequence of 2) and wherein the at least one gene of 3) and the optional oligonucleotide interacting sequence of 4) are placed between the integrase-dependent/resolvase-dependent sequences, and wherein the polynucleotide lacks an origin of replication and a marker gene.

29. A cultured recombinant cell comprising one or more copies of the recombinant DNA according to claim 9 inserted into its genome.

30. A cultured recombinant cell comprising the recombinant DNA according to claim 10.

31. The cultured recombinant cell according to claim 30, wherein said cell is a bacterium.

32. The cultured recombinant cell according to claim 30, wherein said cell is a eukaryotic cell.

33. The cultured recombinant cell according to claim 31, wherein the bacterium is *Escherichia coli* D1210HP with accession number I-2314.

34. A method for preparation of the DNA molecule according to claim 1, comprising culturing 1) a host cell comprising a recombinant DNA comprising a nucleic acid consisting of an expression cassette positioned between two sequences positioned in direct orientation, which recombine by site-specific recombination in the presence of a recombinase, and wherein the expression cassette comprises a gene of interest under control of a transcription promoter and a transcription terminator active in a mammalian cell with 2) a recombinase, whereby site-specific recombination occurs between the two sequences positioned in direct orientation.

35. The method according to claim 34, wherein said expression cassette is positioned between two bacteriophage sequences, which are positioned in direct orientation and recombine by site-specific recombination.

36. The method according to claim 34, wherein the cultured host cell is brought into contact with the recombinase by transfecting or infecting the cultured host cell with a plasmid or a phage containing a gene for the recombinase.

37. The method according to claim 34, wherein the cultured host cell is brought into contact with the recombinase by inducing expression of a gene coding for the recombinase, wherein the gene is present in the host cell.

38. The method according to claim 37, wherein the host cell comprises within its genome a recombinase gene having temperature-regulated expression, and wherein the cultured host cell is brought into contact with the recombinase by culturing the host cell at an induction temperature of the recombinase gene, whereby expression of the recombinase gene is induced.

39. The method according to claim 38, wherein the host cell comprises a lysogenic phage integrated in its genome and wherein the lysogenic phage comprises the gene for the recombinase.

40. A method for preparation of the DNA molecule according to claim 1, comprising combining:
   a) a replicative plasmid comprising:
      1) an origin of replication and optionally, a marker gene; and
      2) a polynucleotide comprising an expression cassette positioned between two sequences positioned in direct orientation, which recombine by site-specific recombination in the presence of a recombinase, wherein the expression cassette comprises a gene of interest under control of a transcription promoter and a transcription terminator active in a mammalian cell, and wherein the polynucleotide lacks an origin of replication and a marker gene; and
   b) a recombinase, whereby site-specific recombination occurs between the two sequences of 2) positioned in direct orientation.

41. The method according to claim 34, further comprising purifying a minicircle formed by said site-specific recombination.

42. The method according to claim 41, wherein the minicircle is purified by contacting the minicircle with a specific oligonucleotide that is grafted onto a support, whereby a triple helix is formed by hybridization of said specific oligonucleotide with a specific sequence present in the minicircle.

43. The recombinant DNA according to claim 9, wherein the two sequences which recombine by site-specific recombination are from a 2μ plasmid.

* * * * *

SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
      (A) LENGTH: 37 base pairs
      (B) TYPE: nucleic acid
      (C) STRANDEDNESS: double
      (D) TOPOLOGY: linear (ii) MOLECULE TYPE: other nucleic acid
            (A) DESCRIPTION: /desc = "Oligonucleotide"

(xi) SEQUENCE DESCRIPTION: SEQ ID NO:1:

AATTGTGAAG CCTGCTTTTT TATACTAACT TGAGCGG                                     37

(2) INFORMATION FOR SEQ ID NO:2:

(i) SEQUENCE CHARACTERISTICS:
        (A) LENGTH: 37 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:2:

AATTCCGCTC AAGTTAGTAT AAAAAAGCAG GCTTCAC                                     37

(2) INFORMATION FOR SEQ ID NO:3:

(i) SEQUENCE CHARACTERISTICS:
        (A) LENGTH: 57 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:3:

GATCCGAAGA AGAAGAAGAA GAAGAAGAAG AAGAAGAAGA AGAAGAAGAA GAAGAAC              57

(2) INFORMATION FOR SEQ ID NO:4:

(i) SEQUENCE CHARACTERISTICS:
        (A) LENGTH: 57 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:4:

GATCGTTCTT CTTCTTCTTC TTCTTCTTCT TCTTCTTCTT CTTCTTCTTC TTCTTCG              57

(2) INFORMATION FOR SEQ ID NO:5:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:5:

GAGGCTTCTT CTTCTTCTTC TTCTT                                                 25

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: other nucleic acid
            (A) DESCRIPTION: /desc = "Oligonucleotide"

(xi) SEQUENCE DESCRIPTION: SEQ ID NO:6:

CTGCTTTTTT ATACTAACTT G                                              21

(2) INFORMATION FOR SEQ ID NO:7:

(i) SEQUENCE CHARACTERISTICS:
            (A) LENGTH: 21 base pairs
            (B) TYPE: nucleic acid
            (C) STRANDEDNESS: double
            (D) TOPOLOGY: linear (ii) MOLECULE TYPE: other nucleic acid
            (A) DESCRIPTION: /desc = "Oligonucleotide"

(xi) SEQUENCE DESCRIPTION: SEQ ID NO:7:

CAGCTTTTTT ATACTAAGTT G                                              21

(2) INFORMATION FOR SEQ ID NO:8:

(i) SEQUENCE CHARACTERISTICS:
            (A) LENGTH: 21 base pairs
            (B) TYPE: nucleic acid
            (C) STRANDEDNESS: double
            (D) TOPOLOGY: linear (ii) MOLECULE TYPE: other nucleic acid
            (A) DESCRIPTION: /desc = "Oligonucleotide"

(xi) SEQUENCE DESCRIPTION: SEQ ID NO:8:

CAGCGCATTC GTAATGCGAA G                                              21

(2) INFORMATION FOR SEQ ID NO:9:

(i) SEQUENCE CHARACTERISTICS:
            (A) LENGTH: 21 base pairs
            (B) TYPE: nucleic acid
            (C) STRANDEDNESS: double
            (D) TOPOLOGY: linear (ii) MOLECULE TYPE: other nucleic acid
            (A) DESCRIPTION: /desc = "Oligonucleotide"

(xi) SEQUENCE DESCRIPTION: SEQ ID NO:9:

CTTATAATTC GTAATGCGAA G                                              21

(2) INFORMATION FOR SEQ ID NO:10:

(i) SEQUENCE CHARACTERISTICS:
            (A) LENGTH: 19 base pairs
            (B) TYPE: nucleic acid
            (C) STRANDEDNESS: double
            (D) TOPOLOGY: linear (ii) MOLECULE TYPE: other nucleic acid
            (A) DESCRIPTION: /desc = "Oligonucleotide"

(xi) SEQUENCE DESCRIPTION: SEQ ID NO:10:

AACACTTTCT TAAATGGTT                                                 19

(2) INFORMATION FOR SEQ ID NO:11:

(i) SEQUENCE CHARACTERISTICS:
            (A) LENGTH: 19 base pairs
            (B) TYPE: nucleic acid
            (C) STRANDEDNESS: double (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:11:

AACACTTTCT TAAATTGTC                                                        19

(2) INFORMATION FOR SEQ ID NO:12:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:12:

AAGGGATTTA AAATCCCTC                                                        19

(2) INFORMATION FOR SEQ ID NO:13:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:13:

ATGGTATTTA AAATCCCTC                                                        19

(2) INFORMATION FOR SEQ ID NO:14:

(i) SEQUENCE CHARACTERISTICS:
        (A) LENGTH: 49 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:14:

TTCTCTGTCG GGGTGGCGGG ATTTGAACCC ACGACCTCTT CGTCCCGAA                        49

(2) INFORMATION FOR SEQ ID NO:15:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:15:

CGTCGAAATA TTATAAATTA TCAGACA                                               27

(2) INFORMATION FOR SEQ ID NO:16:

(i) SEQUENCE CHARACTERISTICS:
        (A) LENGTH: 66 base pairs
        (B) TYPE: nucleic acid (C) STRANDEDNESS: double
            (D) TOPOLOGY: linear (ii) MOLECULE TYPE: other nucleic acid
            (A) DESCRIPTION: /desc = "Oligonucleotide"

(xi) SEQUENCE DESCRIPTION: SEQ ID NO:16:

GATCTGAAGA AGAAGAAGAA GAAGAAGAAG AAGAAGAAGA AGAAGAAGAA GAAGAACTGC        60

AGATCT        66

(2) INFORMATION FOR SEQ ID NO:17:

(i) SEQUENCE CHARACTERISTICS:
            (A) LENGTH: 66 base pairs
            (B) TYPE: nucleic acid
            (C) STRANDEDNESS: double
            (D) TOPOLOGY: linear (ii) MOLECULE TYPE: other nucleic acid
            (A) DESCRIPTION: /desc = "Oligonucleotide"

(xi) SEQUENCE DESCRIPTION: SEQ ID NO:17:

GATCAGATCT GCAGTTCTTC TTCTTCTTCT TCTTCTTCTT CTTCTTCTTC TTCTTCTTCT        60

TCTTCA        66

(2) INFORMATION FOR SEQ ID NO:18:

(i) SEQUENCE CHARACTERISTICS:
            (A) LENGTH: 57 base pairs
            (B) TYPE: nucleic acid
            (C) STRANDEDNESS: double
            (D) TOPOLOGY: linear (ii) MOLECULE TYPE: other nucleic acid
            (A) DESCRIPTION: /desc = "Oligonucleotide"

(xi) SEQUENCE DESCRIPTION: SEQ ID NO:18:

GATCAGATCT GCAGTCTCTT CTTCTTCTTC TTCTTCTTCT TCTTCTTCTC TTCTTCA        57

(2) INFORMATION FOR SEQ ID NO:19:

(i) SEQUENCE CHARACTERISTICS:
            (A) LENGTH: 21 base pairs
            (B) TYPE: nucleic acid
            (C) STRANDEDNESS: double
            (D) TOPOLOGY: linear (ii) MOLECULE TYPE: other nucleic acid
            (A) DESCRIPTION: /desc = "Oligonucleotide"

(xi) SEQUENCE DESCRIPTION: SEQ ID NO:19:

CTTCTTCTTC TTCTTCTTCT T        21

(2) INFORMATION FOR SEQ ID NO:20:

(i) SEQUENCE CHARACTERISTICS:
            (A) LENGTH: 56 base pairs
            (B) TYPE: nucleic acid
            (C) STRANDEDNESS: double
            (D) TOPOLOGY: linear (ii) MOLECULE TYPE: other nucleic acid
            (A) DESCRIPTION: /desc = "Oligonucleotide"

(xi) SEQUENCE DESCRIPTION: SEQ ID NO:20:

AGCTTCTCGA GCTGCAGGAT ATCGAATTCG GATCCTCTAG AGCGGCCGCG AGCTCC        56

```
(2) INFORMATION FOR SEQ ID NO:21:

(i) SEQUENCE CHARACTERISTICS:
        (A) LENGTH: 56 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:21:

AGCTGGAGCT CGCGGCCGCT CTAGAGGATC CGAATTCGAT ATCCTGCAGC TCGAGA            56

(2) INFORMATION FOR SEQ ID NO:22:

(i) SEQUENCE CHARACTERISTICS:
        (A) LENGTH: 49 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:22:

ACTAGTGGCC ATGCATCCGC TCAAGTTAGT ATAAAAAAGC AGGCTTCAG                    49

(2) INFORMATION FOR SEQ ID NO:23:

(i) SEQUENCE CHARACTERISTICS:
        (A) LENGTH: 57 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:23:

AGCTCTGAAG CCTGCTTTTT TATACTAACT TGAGCGGATG CATGGCCACT AGTAGCT           57

(2) INFORMATION FOR SEQ ID NO:24:

(i) SEQUENCE CHARACTERISTICS:
        (A) LENGTH: 29 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:24:

GCGTCTAGAA CAGTATCGTG ATGACAGAG                                          29

(2) INFORMATION FOR SEQ ID NO:25:

(i) SEQUENCE CHARACTERISTICS:
        (A) LENGTH: 29 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:25:

GCCAAGCTTA GCTTTGCACT GGATTGCGA                                          29
```